United States Patent
Reder et al.

(10) Patent No.: US 6,231,886 B1
(45) Date of Patent: *May 15, 2001

(54) METHODS OF PROVIDING SUSTAINED TREATMENT WITH OPIOIDS

(76) Inventors: Robert F. Reder, 2 Mercia La., Greenwich, CT (US) 06830; Paul D. Goldenheim, 4 Bald Hill Pl., Wilton, CT (US) 06897; Robert F. Kaiko, 10 Norfield Woods Rd., Weston, CT (US) 06883

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/311,997

(22) Filed: May 14, 1999

Related U.S. Application Data

(63) Continuation of application No. 08/939,068, filed on Sep. 29, 1997, now Pat. No. 5,688,547.
(60) Provisional application No. 60/038,919, filed on Feb. 24, 1997.

(51) Int. Cl.$^7$ ......................................................... A61K 9/70
(52) U.S. Cl. ........................... 424/449; 424/443; 424/446; 424/447
(58) Field of Search ................................. 424/489, 400, 424/449, 446, 447, 443

(56) References Cited

U.S. PATENT DOCUMENTS

| | | | |
|---|---|---|---|
| 3,996,934 | 12/1976 | Zaffaroni | 128/268 |
| 4,060,084 | 11/1977 | Chandrasekaren et al. | 128/260 |
| 4,262,003 | 4/1981 | Urquart et al. | 424/267 |
| 4,379,454 | 4/1983 | Cambell et al. | 604/897 |
| 4,588,580 | 5/1986 | Gale et al. | 424/21 |
| 4,806,341 | 2/1989 | Chien et al. | 424/448 |
| 4,906,463 | 3/1990 | Cleary | 424/78 |
| 4,908,027 | 3/1990 | Enscore et al. | 604/890.1 |
| 4,983,395 | 1/1991 | Chang et al. | 424/448 |
| 5,026,556 | 6/1991 | Drust et al. | 424/449 |
| 5,069,909 | 12/1991 | Sharma et al. | 424/449 |
| 5,132,115 | 7/1992 | Wolter | 424/448 |
| 5,225,199 | 7/1993 | Hidaka et al. | 424/443 |

(List continued on next page.)

FOREIGN PATENT DOCUMENTS

| | | | |
|---|---|---|---|
| 3526339 | 1/1992 | (DE) | A61L/15/44 |
| 3546830 | 7/1995 | (DE) | A61L/15/44 |
| 0368409 | 5/1990 | (EP) | A61K/31/485 |
| 2165148 | 5/1989 | (GB) | A61K/9/70 |
| 9619975 | 12/1994 | (WO) | |

OTHER PUBLICATIONS

Hihuchi, William I., Ph.D., et al., "Particle Phenomena and Coarse Dispersions", Chapter 21, p. 294.
Colloidal Dispersions, p. 267.
Chien, pp. 31–44, col. 8 and 9.
Climara® Product Information, Physician's Desk Reference (1998) pp. 672–676.
Catapres TTS® Product Information, Physicians' Desk Reference (1998) pp. 610–612.

(List continued on next page.)

Primary Examiner—Thurman K. Page
Assistant Examiner—Blessing Fubara
(74) Attorney, Agent, or Firm—Davidson, Davidson & Kappel

(57) ABSTRACT

A method of effectively treating pain in humans is achieved by administering buprenorphine in accordance with first order kinetics over an initial three-day dosing interval, such that a maximum plasma concentration from about 20 pg/ml to about 1052 pg/ml is attained, and thereafter maintaining the administration of buprenorphine for at least an addition two-day dosing interval in accordance with substantially zero order kinetics, such that the patients experience analgesia throughout the at least two-day additional dosing interval.

11 Claims, 5 Drawing Sheets

U.S. PATENT DOCUMENTS

| | | | |
|---|---|---|---|
| 5,240,711 | 8/1993 | Hille et al. ............................. | 424/448 |
| 5,336,210 | 8/1994 | Hidaka et al. ........................ | 604/307 |
| 5,462,745 | 10/1995 | Enscore et al. ....................... | 424/448 |
| 5,486,362 | 1/1996 | Kitchell ................................. | 424/426 |
| 5,613,958 | 3/1997 | Kochinke et al. .................... | 604/307 |
| 5,635,203 | 6/1997 | Gale et al. ............................. | 424/448 |
| 5,732,717 * | 3/1998 | Watanabe et al. .................... | 128/898 |

OTHER PUBLICATIONS

Sustained oral mucosal delivery in human volunteers of buprenorphine from a thin non–eroding mucoadhesive polymeric disk, R.L.McQuinn, et al., Journal of Controlled Release 34 (1995) 243–250.

Scale–up of Adhesive Transdermal Drug Delivery Systems, Glenn A. Van Buskirk, et al., Phamaceutical Research, vol. 14, No. 7, 1997.

Buprenorphine: Differential Interaction with Opiate Receptor Subtypes in Vivo, Wolfgang Sadée, et al., The Journal of Pharmacology and Experimental Therapeutics, Copyright ® 1982, vol. 223, No. 1, pp. 157–162.

Human Pharmacokinetics of Intravenuous, Sublingual and Buccal Buprenorphine*, James J. Kuhlman, Jr., et al., Journal of Analytical Toxicology, vol. 20, Oct. 1996.

Transdermal Delivery of Buprenorphine through Cadaver Skin, Samir D. Roy, et al., Journal of Pharmaceutical Sciences, vol. 83, No. 2, Feb. 1994, pp. 126–130.

Pharmacokinetic evaluation of transdermal buprenorphine in man, I.R. Wilding, et al., International Journal of Pharmaceutics 132 (1996) 81–87.

* cited by examiner

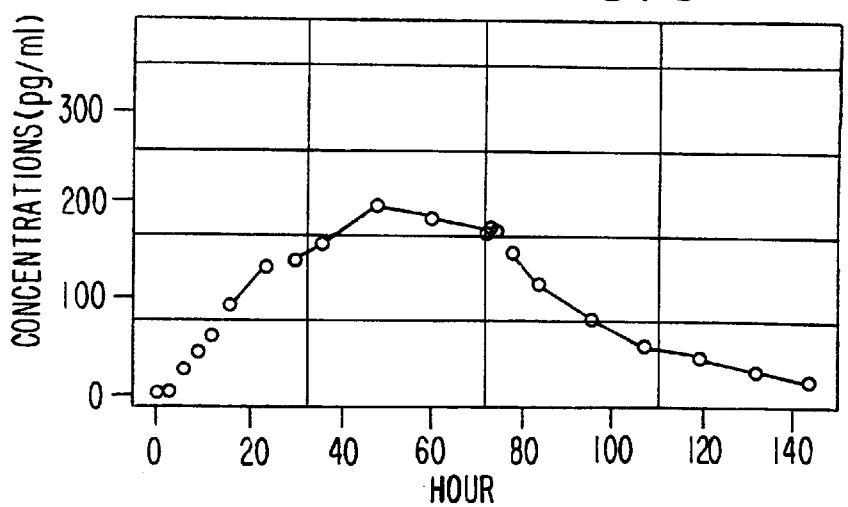
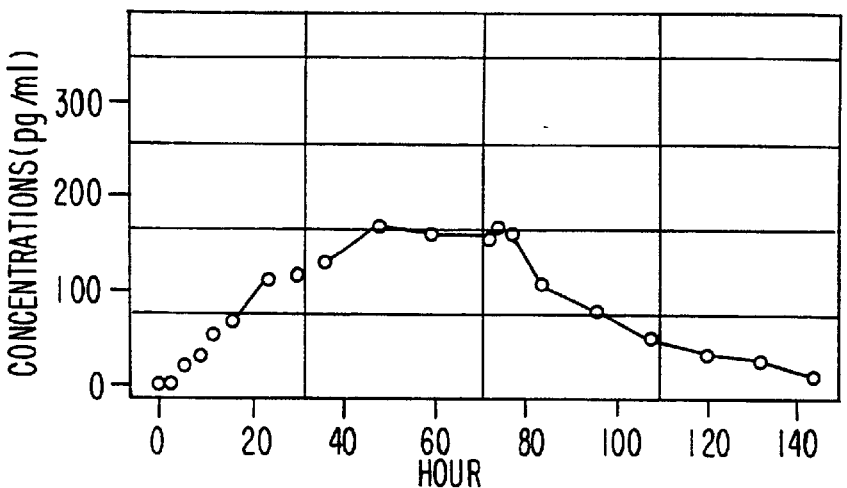
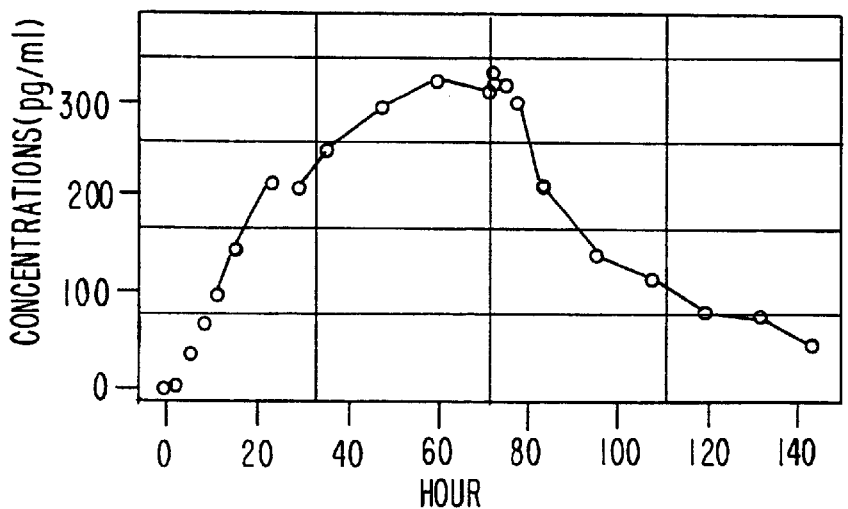

METHODS OF PROVIDING SUSTAINED TREATMENT WITH OPIOIDS

This application is a continuation of Ser. No 08/939,068, filed Sep. 29, 1997 now U.S. Pat No. 5,688,547 Provisional Application No. 06/038,919 filed Feb. 24, 1997.

BACKGROUND OF THE INVENTION

It is the intent of all sustained-release pharmaceutical preparations to provide a longer period of pharmacologic effect after the administration of a drug than is ordinarily experienced after the administration of immediate release preparations of the same drug. Such longer periods of efficacy can provide many inherent therapeutic benefits that are not achieved with corresponding immediate release preparations. The benefits of prolonged analgesia afforded by sustained release oral analgesic preparations have become universally recognized and oral opioid analgesic sustained-release preparations are commercially available.

Prolonged analgesia is particulary desirable in patients suffering from moderate to severe pain, such as cancer patients. Available oral preparations provide a duration of effect lasting e.g., about twelve hours (and sometimes 24 hours) such that a drug may only have to be administered to a patient one to three times a day. For example, morphine, which has been considered to be the prototypic opioid analgesic, has been formulated into twice-daily, oral controlled release formulations (e.g., MS Contin® tablets, commercially available from The Purdue Frederick Company).

Another approach to sustained delivery of a therapeutically active agent are transdermal delivery systems, such as transdermal patches. Generally, transdermal patches contain a therapeutically active agent (e.g., an opioid analgesic), a reservoir or matrix containing the opioid or other active ingredient(s) and an adhesive which allows the transdermal device to adhere to the skin, allowing for the passage of the active agent from the device through the skin of the patient. Once the active agent has penetrated the skin layer, the drug is absorbed into the blood stream where it can exert a desired pharmacotherapeutic effect, such as analgesia.

Transdermal delivery systems in which an opioid analgesic is the active ingredient have been contemplated. For example, a commercially available opioid analgesic transdermal formulation is Duragesic® (commercially available from Janssen Pharmaceutical; active ingredient is fentanyl). The Duragesic® patch is said to provide adequate analgesia for up to 48 to 72 hours (2 to 3 days).

Buprenorphine, a partially synthetic opiate, has also been contemplated for prolonged analgesia. Although other types of opioid analgesic transdermal formulations have been reported in the literature (such as fentanyl, discussed above), buprenorphine transdermal delivery systems are of particular interest because buprenorphine is a potent, partial agonist opioid analgesic with desirable therapeutic properties. For example, buprenorphine is 50 to 100 times more potent than morphine, but has a much safer therapeutic index than morphine (see Wallenstein S L, et al., Crossover Trials in Clinical Analgesic Assays: Studies of Buprenorphine and Morphine, Pharmacotherapy, G(5): 225–235, 1986 hereby incorporated by reference). Further, the partial agonist properties of buprenorphine are useful in the treatment of opioid addiction.

There are several types of transdermal formulations of buprenorphine reported in the literature. See, for example, U.S. Pat. No. 5,240,711 (Hille et al.), U.S. Pat. No. 5,225,199 (Hidaka et al.), U.S. Pat. No. 5,069,909 (Sharma et al.), U.S. Pat. No. 4,806,341 (Chien et al.), and U.S. Pat. No. 5,026,556 (Drust et al.), all of which are hereby incorporated by reference.

Buprenorphine has a low oral bioavailability and has been considered by certain of those skilled in the art to be like other narcotics which are habit-forming (see, e.g., U.S. Pat. No. 5,240,711 to Hille, et.al.) and induce tolerance (see, e.g., U.S. Pat. No. 5,613,958 to Kochinke, et. al.). As reported in Hille, et.al., experts are of the opinion that the form of administration of a medicinal drug contributes to the risk of addiction, and higher than necessary blood levels created immediately after administration of a drug such as buprenorphine, followed by a drastic decrease (causing in succession euphoria and then ineffective pain treatment), cause the patient to start to long for the next dosage (referred to as an "iatrogenic" addiction). In the case of buprenorphine, Hille, et al. reported that continuous infusion would be considered the most suitable mode to avoid such an iatrogenic addition by providing constant blood levels; however, continuous infusion requires physician control and insertion of a cannula (which may cause inflammation at the site). This problem is considered to be overcome by Hille, et al. by virtue of their use of a transdermal delivery system which includes buprenorphine or one of its pharmaceutically compatible salts and which releases the drug over a period of at least 24 hours in a controlled manner, and ensures that the buprenorphine does not notably decompose when the transdermal delivery system is stored, and which further ensures that the buprenorphine in-vivo penetrates through the skin at the required amount.

Kochinke et al. describe a transdermal system for the modulated administration of tolerance-inducing drugs. Buprenorphine is identified therein as such a drug. The system is designed to deliver the drug through the patient's skin via a three-phase drug delivery profile. In the first phase, which begins with patch application and ends at 2–10 hours after patch application, plasma levels of the drug are obtained. This phase is followed by a second phase in which therapeutic plasma levels of the drug are maintained. The second phase begins at about two to ten hours after patch application and ends at about 8–18 hours after patch application. In a third phase, sub-therapeutic levels of the drug are maintained, via inherent patch design and/or patch removal. The rationale behind the drug delivery profile of Kochinke et al. is that initial high blood levels may be more effective when followed by a period of decreasing dosage (down to sub-therapeutic levels), than if the blood levels are maintained either at the higher or lower level (i.e., sub-therapeutic levels) throughout the entire administration period. By virtue of this modulated profile, it is said that the onset of tolerance to the drug being administered can be prevented or greatly reduced.

Despite these advances in the art, there remains a need for methods of treating patients with buprenorphine that provide effective analgestic levels of buprenorphine for prolonged periods of time while eliminating or minimizing dependence, tolerance, and side effects, thus providing a safe and effective method of pain management.

OBJECTS AND SUMMARY OF THE INVENTION

It is an object of the present invention to provide a method which allows for reduced plasma concentrations of buprenorphine over a prolonged time period than possible according to prior art methods, while still providing effective pain management.

It is a futher object of the present invention to provide a method for treating patients in pain with buprenorphine which achieves prolonged and effective pain management, while at the same time provides the opportunity to reduce side effects, dependence and tolerance which the patients may experience when subjected to prolonged treatment with a narcotic such as buprenorphine.

It is yet a further object to provide a method for the treatment of pain in patients by utilizing a transdermal delivery system which contains buprenorphine in a manner which maximizes the dosage interval, i.e., the interval during which the transdermal delivery system is maintained in contact with the skin, and minimizes the plasma concentrations in the patients during the dosage interval, while surprisingly maintaining effective pain management.

A further object of the invention is to provide a method for treating opioid-addicted patients in a manner which gradually reduces the plasma concentration of opioid in the patients' plasma while at the same time providing effective plasma concentrations for those patients to be detoxified.

The invention is directed in part to the surprising result that effective pain management is provided by providing a substantially first order rate of increase of blood plasma concentrations of buprenorphine over about a three day (e.g., 72 hours) time interval, followed by a prolonged time period of at least about two days (e.g., 48 hours) during which the plasma concentrations of buprenorphine are maintained according to substantially zero order pharmacokinetics.

In accordance with the above objects and others, the invention relates in part to a method of effectively treating pain in humans, comprising administering buprenorphine to human patients in a manner such that the following mean plasma concentrations are achieved over a 72 hour dosing interval: a mean plasma concentration from about 0.3 to about 113 pg/ml at about 6 hours after initiation of the dosing interval; a mean plasma concentration from about 3 to about 296 pg/ml at about 12 hours after initiation of the dosing interval; a mean plasma concentration from about 11 to about 644 pg/ml at about 24 hours after initiation of the dosing interval; a mean plasma concentration from about 13 to about 630 pg/ml at about 30 hours after initiation of the dosing interval; a mean plasma concentration from about 15 to about 715 pg/ml at about 36 hours after initiation of the dosing interval; a mean plasma concentration from about 20 to about 984 pg/ml at about 48 hours after initiation of the dosing interval; a mean plasma concentration from about 21 to about 914 pg/ml at about 60 hours after initiation of the dosing interval; a mean plasma concentration from about 24 to about 850 pg/ml at about 72 hours after initiation of the dosing interval; and thereafter administering the buprenorphine in a manner such that the mean plasma concentrations are mntained from about 19 to about 850 pg/ml over at least the next 48 hours. In certain preferred embodiments, the dosing interval is maintained over a seven day period.

Any mode of admiration may be utilized to attain the above plasma concentrations over time. For example, the buprenorphine may be administered transdermally, parenterally, sublingually, orally, buccally, rectally, etc. Oral bioavailability of buprenorphine is very low (estimated as 15%). In order to better control plasma concentrations of buprenorphine within the concentrations desired in the herein-described inventive methods, it is preferred that the buprenorphine is administered via a transdermal delivery system or via continuous infusion.

In a further preferred embodiment of the invention, the method comprises applying a transdermal delivery system containing buprenorphine as the active ingredient onto the skin of patients which provide a release rate of buprenorphine over about a 72 hour dosing interval such that a maximum plasma concentration from about 20 pg/ml to about 850 pg/ml is attained (depending upon the dosage levels needed to maintain analgesia in the particular patients), and then maintaining the transdermal delivery systems on the skin of the patients for at least an additional 24 hour interval during which the plasma concentrations of buprenorphine in the patients are maintained above minimum effective concentrations of the drug and the patients continue to experience effective pain management during this additional dosing interval.

The invention is further directed to a method of effectively treating pain in humans, comprising administering buprenorphine transdermally to human patients such that mean relative release rates are achieved as follows: a mean relative release rate of from about 3 ug/hr to about 86 ug/hr from initiation of the dosing interval until about 72 hours thereafter; and a mean relative release rate of about 0.3 ug/hr to about 9 ug/hr from about 72 hours after the initiation of the dosing interval until at least about 120 hour hours after the initiation of the dosing interval. In certain preferred embodiments, the mean relative release rate of about 0.3 ug/hr to about 9 ug/hr is maintained from about 72 hours after the initiation of the dosing interval until at least about 168 hours after the initiation of the dosing interval.

The present invention is further related to a method of effectively treating pain in humans, comprising administering buprenorphine transdermally to human patients such that a mean relative release rate from about 3 ug/hr to about 86 ug/hr of buprenorphine is achieved until about 72 hours after the application of a transdermal delivery system, and therafter providing (either with the same transdermal delivery system or upon removal of the system and replacement with a different transdermal delivery system) a mean relative release rate of about 0.3 ug/hr to about 9 ug/hr from about 72 hours after the initiation of the dosing interval until at least about 120 hours after the initiation of the dosing interval, and preferably until at least about 168 hours after the initiation of the dosing interval.

In preferred embodiments, the nethod comprises the application of a transdermal delivery system which is designed to be provide analgesia for about 72 hours, and which provides a release rate of the drug when applied to the skin which generally follows first order pharmacokinetics over that 72 hour period, and further comprises taking advantage of the fact that such transdermal delivery systems typically provide a dramatic drop-off in the release rate of buprenorphine after the first 72 hours, but nevertheless provide a relatively small but sufficient release of buprenorphine to maintain analgesia and desirable plasma concentrations in the patients over a further period of time of at least, e.g., preferably at least 48 hours, by leaving the transdermal delivery system in contact with the skin of the patient for such additional desired dosing interval, which may be as long as, e.g., an additional 96 hours or more. Surprisingly, it has been found that such transdermal dosage systems exhibit substantially zero order release after about the initial 72 hour dosage interval, and therefore are capable of maintaining effective plasma concentrations of buprenorphine for a much longer period than previously reported in the prior art. However, the inventive method also contemplates the possibility of utilizing a first transdermal delivery system which provides the desired substantially first order kinetics, and therefter the removal of the first transdermal delivery system and its replacement with a second system which provides the desired substantially zero order pharmacokinetics for a prolonged period of time (e.g., at least about 24 hours, preferably at least about 48 hours, and most preferably about 96 hours). This second system may be a second transdermal delivery system which provides the afore-mentioned mean relative release rate of about 0.3 ug/hr to about 9 ug/hr. On the other hand, the second system may even utilize a different miode of administration, for example, continuous infusion.

The present invention is also related, in part, to a method of effectively treating pain in patients, comprising applying onto the skin of the patients a transdermal delivery system containing buprenorphine which transdermal delivery system delivers the buprenorphine substantially according to first order kinetics to provide a mean plasma concentration from about 24 to about 850 pg/ml about 3 days after application, and then maintaining the transdermal buprenorphine formulation in contact with the skin of the human patient for about 2 to about 6 additional days without removing the transdermal formulation, such that the patient continues to receive effective analgesia from the transdermal buprenorphine formulation.

The invention also provides, in certain preferred embodiments, an improvement in a method of treating pain in human patients by applying a 3 day transdermal delivery system containing buprenorphine onto the skin of the patient and maintaining the transdermal delivery system in contact with the skin for a 3 day dosing interval, the transdermal delivery system containing an amount of buprenorhpine sufficient to provide effective analgesia in the patient for about 3 days, the improvement comprising maintaining the transdermal dosage form in contact with the patient's skin for at least 2 to about 6 additional days beyond the 3 day dosing interval.

The present invention also relates to a method of treating opioid addiction by administering buprenorphine transdermally to human patients which provides a release rate of the drug when applied to the skin which generally follows first order pharmacokinetics over a 72 hour period, such that the addict attains a buprenorphine plasma concentration from about 1000 to about 10,000 µg/ml, and preferably from about 5000 to about 8000 µg/ml, about 72 hours after application of a buprenorphine transdermal delivery system, and thereafter maintaining the transdennal delivery system in contact with the skin of the addict such that a mean relative release rate of buprenorphine approximating zero order kinetics over an additional dosing interval of at least about 48 hours, to provide the desired therapeutic effect (detoxification). In preferred embodiments the transdermal delivery system is maintained in contact with the addict's skin for about 7 days.

The methods of the present invention are described in further detail in the following sections. However, it should be understood that for purposes of the present invention, the following terms have the following meanings:

The term "effective analgesia" is defined for purposes of the present invention as a satisfactory reduction in or elimination of pain, along with the process of a tolerable level of side effects, as determined by the human patient.

The term "effective pain management" means for purposes of the present invention as the objective evaluation of a human patient's response (pain experienced versus side effects) to analgesic treatment by a physician as well as subjective evaluation of therapeutic treatment by the patient undergoing such treatment. The skilled artisan will understand that effective analgesia will vary according to many factors, including individual patient variations.

The term "breakthrough pain" means pain which the patient experiences despite the fact that the patient is being administered generally effective amounts of, e.g., an opioid analgetic such as buprenorphine.

The term "rescue" refers to a dose of an analgesic which is administered to a patient experiencing breakthrough pain.

The term "first order" pharmacokinetics is defined as plasma concentrations which increase over a specified time period. Drug release from suspension matrices according to first order kinetics may be defined as follows:

Amount released per area unit $Q = \sqrt{D_{eff}(2 \cdot C_0 - C_s) \cdot C_s \cdot t}$
(First order kinetics)

$$D_{eff} = \text{apparent diffusion coefficient} \frac{M}{\sqrt{t}} = 2 \cdot C_o \cdot \sqrt{D_{eff}/n}$$

$C_0$=initial drug concentration in the transdermal delivery system
$C_s$=saturation concentration
t=time
Assumptions: perfect sink; diffusion of dissolved drug is rate controlling; therefore $$Q = \text{const} \cdot \sqrt{t}$$

Drug release from solution matrices according to first order kinetics may be defined as follows:

Amount released per area unit $Q =$ $$\sqrt{2 \cdot C_o} \left( Deff \cdot \frac{t}{\pi} \right) \text{ (First order kinetics)}$$

Assumptions: perfect sink; diffusion of dissolved drug is rate controlling: $M_1 \leq 0.4 M_0$ therefore $Q = \text{const} \cdot \sqrt{t}$.

The term "zero order" pharamacokinetics contemplates an amount of drug released from a buprenorphine formulation which substanially maintains plasma concentrations at a relatively constant level. For purposes of the present invention, a relatively constant plasma concentration is defined as a concentration which does not decrease more than about 30% over a 48 hour time period.
Drug release from membrane-controlled systems may be defined as follows:

Amount released per area unit Q=const (zero order dinetics)

The term "mean relative release rate" is determined from the amount of drug released per unit time from the transdermal delivery system through the skin and into the bloodstream of a human patient. Mean relative release rate may be expressed, e.g. as µg drug/cm²/hr. For example, a transdermal delivery system that release 1.2 mg of buprenorphine wver a time peroid of 72 hours is considered to have a relative rate of 16.67 µg/hr. For purpose of the invention, it is understood that relative release rates may change between any paticular time points within a particular dosing interval, and the term therefore only reflects the overall release rate during the particular dosing interval. For purpose of the present invention, relative release rate should be considered sunonomous with the term "flux rate".

The term "sustained release" is defined for purposes of the purposes of the present as the release of the drug (opioid analgesic) from the transdermal formulation at such a rate that blood (e.g., plasma) concentration (levels) are maintained within the therapeutic range (above the minimium effective analgesic concentration or "MEAC") but below toxic levels over a period of time of about 3 days or longer.

The term "steady state" means that the blood plasma concentration curve for a given drug has been substantially repeated from dose to dose.

The term "minimum effective analgesic concentration" is defined for purposes of this invention as the minimum effective therapeutic blood plasma level of the drug at which at least some pain relief is achieved in a given patient. It will be well understood by those skilled in the medical art that pain measurement is highly subjective and great individual variations may occur among patients.

For purposes of the present invention, the term "buprenorphine" shall include buprenorphine base, pharmaceutically acceptable salts thereof, stereoisomers thereof, ethers and esters thereof, and mixtures thereof.

The term "overage" means for the purposes of the present invention the amount of buprenorphine contained in a transdermal delivery system which is not delivered to the patient. The overage is necessary for creating a concentration gradient by means of which the active agent (e.g., buprenorphine) migrates through the layers of the transdermal dosage form to the desired site on a patient's skin.

BRIEF DESCRIPTION OF THE DRAWINGS

The following drawings are illustrative of embodiments of the invention and are not meant to limit the scope of the invention as encompassed by the claims.

FIG. 9 is a graphical representation of the plasma concentration (pg/ml) over time (hours) for Comparative Example D;

FIG. 10 is a graphical representation of the plasma concentration (pg/ml) over time (hours) for Comparative Example E;

FIG. 11 is a graphical representation of the plasma concentration (pg/ml) over time (hours) for Comparative Example F;

DETAILED DESCRIPTION

Figure 1:
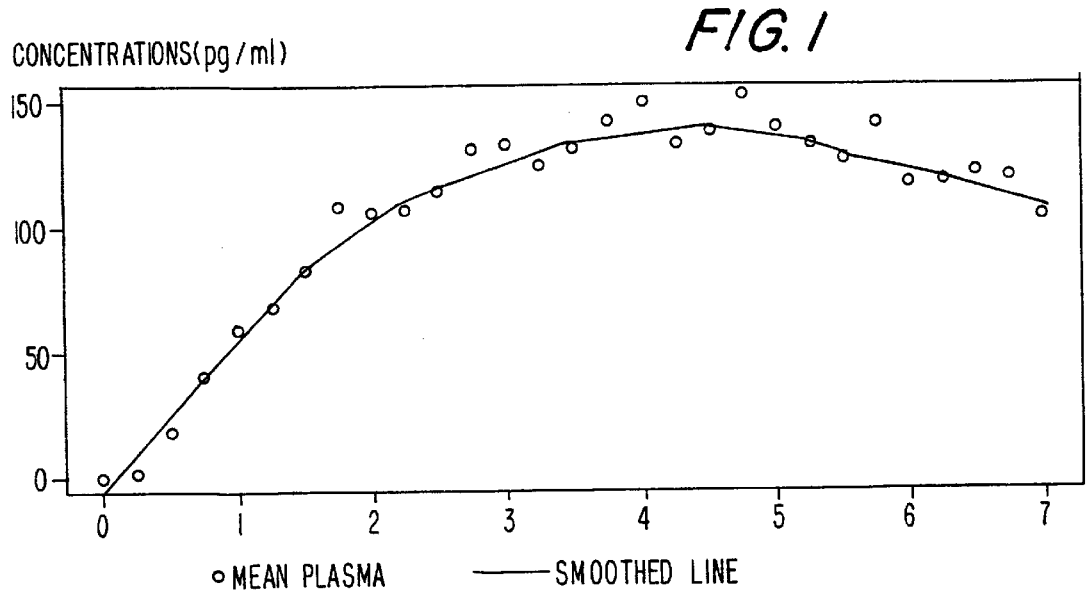
FIG. 1 is a graphical representation of the mean plasma concentration (pg/ml) versus time (days) for Example 1.

While chronic pain is often manageable with the use of the combination of "mild" analgesics, and nonpharmacologic interventions, selected patients continue to experience unacceptably intense pain. Some patients with chronic pain cannot tolerate therapeutic doses of "mild" analgesics, while others develop pain of such severity that "strong" analgesics should be considered for subacute or chronic use.

The phrase "strong analgesics" encompasses, inter alia, several classes of opioid analgesics, including the partial agonists. Parenteral buprenorphine (a Schedule V drug under the Controlled Substances Act) is the only example of a partial agonist opioid analgesic currently marketed in the United States.

Partial agonists provide several therapeutic advantages in many patients when compared to morphine-like agonists and mixed agonists-antagonists. For example, unlike the mixed agonists-antagonists (e.g., pentazocine, butorphanol, nalbuphine), buprenorphine is devoid of psychotomimetic adverse reactions; in comparison with agonists (e.g., morphine and fentanyl), the dose-responsive relationship for respiratory depression with buprenorphine is relatively low and the abuse liability of buprenorphine is less.

The chemical of name of buprenorphine is 21-cyclopropyl-7-[(S)-1-hydroxy-1,2,2-trimethylpropyl]-6,14-endo-ethano-6,7,8,14-tetrahydroorpavine. The molecular weigth of buprenorphine base is 467,7; the empirical formula is $C_{29}H_{41}NO_4$.

The structural formula of buprenorphine is shown below:

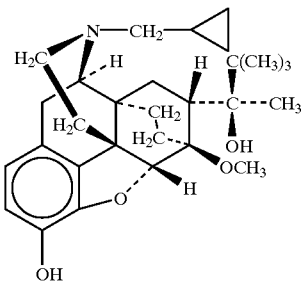

Buprenorphine is an opioid partial agonist and shares many of the actions, such as analgesia, of opioid agonists. A "ceiling effect" to analgesia (i.e., no additional analgesia with increasing dose) is well documented with respect to buprenorphine in many animal models. It is highly lipophilic and dissociates slowly from opioid receptors. Buprenorphine is considered in the art to be a partial agonist at $\mu$ opioid receptors in the central nervous system ("CNS") and peripheral tissues. It is further thought that buprenorphine binds with high affinity to $\mu$ and $\kappa_1$ receptors, and, with lower affinity, to $\delta$ receptors. The intrinsic agonist activity at the $\kappa$ receptor seems to be limited and most evidence suggests that buprenorphine has antagonist activity at $\kappa$ receptors. The lack of $\kappa$ agonism accounts for buprenorphine's freedom from the dysphoric and psychotomimetic effects often seen with agonistlantagonist drugs. Other studies suggest that the opioid antagonist effects of buprenorphine may be mediated via an interaction with $\delta$ opioid receptors.

It is known in the art that buprenorphine binds slowly with, and dissociates slowly from, the $\mu$ receptor. The high affinity of buprenorphine for the $\mu$ receptor and its slow binding to, and dissociation from, the receptor is thought to possibly account for the prolonged duration of analgesia, and in part, for the limited physical dependence potential observed with the drug. The high affinity binding may also account for the fact that buprenorphine can block the $\mu$ agonist effects of other administered opioids.

Like other opioid agonists, buprenorphine produces dose-related analgesia. The exact mechanism has not been fully explained, but analgesia appears to result from a high affinity of buprenorphine for $\mu$ and possibly $\kappa$ opioid receptors in the CNS. The drug may also alter the pain threshold (threshold of afferent nerve endings to noxious stimuli). On a weight basis, the analgesic potency of parenteral buprenorphine appears to be about 25 to about 50 times that of parenteral morphine, about 200 times that of pentazocine, and about 600 times that of meperidine. Buprenorphine may produce sex-related differences in analgesia, with females requiring substantially less drug than males to produce adequate analgesia.

For a study of transdermal delivery of buprenorphine through cadaver skin, see Roy, Samir D. et al., "Transdermal Delivery of Buprenorphine Through Cadaver Skin", *Journal of Pharmaceutical Sciences*, Vol. 83, No. 2, pp. 126–130, (1994), hereby incorporated by reference. For a discussion of buprenorphine pharmacokinetics resulting from application of a fillable transdermal therapeutic system, see Wilding, I. R. et al., "Pharmacokinetic evaluation of transdermal buprenorphine in man," *International Journal of Pharmaceutics*, 132 (1996) pp. 81–87, hereby incorporated by reference. For a discussion of the permeation of buprenorphine and alkyl esters thereof, see Imoto, et al., "Transdermal Prodrug Concepts: Permeation of Buprenorphine and its Alkyl Esters Through Hairless Mouse Skin and Influence of Vehicles," *Biol. Pharm. Bull.*, 19(2)263–267 (1996), hereby incorporated by reference.

Buprenorphine has a low abuse liability compared to fill agonist opioids. Although infrequent, however, buprenorphine may also produce limited physical dependence, and signs and symptoms of mild withdrawal may appear following discontinuance of prolonged therapy with the drug alone. Due to buprenorphine's slow binding with and slow dissociation from the $\mu$ receptor, elimination of the drug from the CNS is prolonged following abrupt discontinuance; consequently, signs and symptoms of acute withdrawal are less intense than those produced by morphine and are delayed in appearance.

In patients physically dependent on opioids, buprenorphine produces many of the subjective and objective effects of opioids; however, the drug may not be a satisfactory substitute for opioid agonists in all patients physically dependent on opioids. Tolerance to the opioid agonist activity of the drug reportedly develops rarely, if at all.

Buprenorphine may produce psychological dependence. Buprenorphine is a partial opioid agonist with behavioral and psychic effects similar to morphine. Unlike pentazocine, however, buprenorphine rarely causes psychotomimetic effects. Like other opioid agonists, buprenorphine may produce increases in cerebrospinal fluid pressure.

The pharmacokinetics of buprenorphine administered parenterally and sublingually are known. Intravenous administration of a single dose of about 0.3 mg of buprenorphine has been shown to provide mean peak plasma drug concentrations of about 18 ng/ml which occur within about 2 minutes; plasma concentrations declined to about 9 and about 0.4 ng/ml after about 5 minutes and about 3 hours, respectively. Following intramuscular administration of a second 0.3-mg dose 3 hours after the initial intravenous dose, mean peak plasma buprenorphine concentrations of about 3.6 ng/ml occur within about 2 to about 5 minutes and decline to about 0.4 ng/ml after about 3 hours. Approximately 10 minutes after administration, plasma concentrations of buprenorphine are similar following intravenous or intramuscular injection.

A parenteral solution of buprenorphine hydrochloride (0.3 mg buprenorphine/ml) is commercially available as Buprenex® (Reckitt & Colman) for intramuscular and intravenous administration. The usual adult dose (over age 13) is 0.3 mg IM or IV every 6 to 8 hours as needed for moderate to severe pain. The pediatric dose in patients age 2 to 12 is 2–6 mcg/kg of body weight every 4–6 hours. The increased frequency of administration in the pediatric population is believed to be caused by increased clearance of buprenorphine compared to the adult population. The mean duration of analgesia generally is six hours following single intramuscular or intravenous doses of 0.2 to 0.3 mg or 2 to 4 $\mu$g/kg; however, in some studies, the mean duration of analgesia reportedly ranged from 4 to 10 hours following single intramuscular doses of 0.2 to 0.6 mg and 2 to 24 hours following single intravenous doses of 0.3 mg or 2 to 15 $\mu$g/kg.

For reference, the mean peak plasma buprenorphine concentration, time to peak concentration, and systemic availability for a 0.4 mg and 0.8 mg single-dose sublingual dose of buprenorphine has been reported by Cowan, Alan and Lewis John, W., *Buprenorphine: Combating Drug Abuse With a Unique Opioids*, Wiley-Liss, Inc., New York, pp. 137–147 (1995), hereby incorporated by reference in its entirety. For a 0.4 mg sublingual dose, the Cmax was reported as 0.50±0.06 ng/ml; the Tmax was reported 210±40 minutes; and a systemic availability of 57.7%±6. For a 0.8 mg sublingual dose, the Cmax was reported as 1.04±1.27 ng/ml; the Tmax was reported 192±49 minutes; and a systemic availability of 54.1%±12.7.

It has previously been reported that a usual sublingual analgesic dose of buprenorphine is 0.2 to 0.4 mg every 8 hours (e.g., Kuhlman, J J et al. *J Analyt Toxicol* 1996; 20(10)). For transdermal patch which might provide a nominal delivery rate of about 12.5 ug/hr, the total buprenorphine administered over a 24 hour period would be about 0.3 mg, and the sublingual equivalent dose over the same period would be about 0.6 mg. For a transdermal delievery system (e.g., a transdermal patch) which might provide a nominal delivery rate of about 25 ug/hr, the total buprenorphine administered over a 24 hour period would be about 0.6 mg, and the sublingual equivalent dose over the same period would be about 1.2 mg. For a transdermal patch which might provide a nominal delivery rate of about 50 ug/hr, the total buprenorphine administered over a 24 hour period would be about 1.2 mg, and the sublingual equivalent dose over the same period would be about 2.4 mg. It is contemplated that one of ordinary skill in the art will appreciate that by simple pharmaceutical calculations, the equivalent doses for achieving the inventive buprenorphine plasma concentration set forth herein can be determined regardless of the mode of administration. In the present discussion, the comparison is made between transdermal dose and sublingual dose.

Distribution of buptenorphine into human body tissues and fluids has not been well characterized. Following oral or intramuscular administration in rats, buprenorphine distributes into the liver, brain, placenta, and GI tract; highest concentrations were attained in the liver within 10 or 40 minutes following oral or intramuscular administration, respectively. The hepatic extraction ratio of buprenorphine is approximately 1. The drug and its metabolites are distributed into bile. Following intravenous administration in humans, the drug rapidly distributes into cerebro spinal fluid ("CSF") (within several minutes). CSF buprenorphine concentrations appear to be approximately 15% to 25% of concurrent plasma concentrations. Buprenorphine is approximately 96% bound to plasma proteins, mainly to and β globulins; the drug does not appear to bind substantially to albumin.

Buprenorphine is almost completely metabolized in the liver, principally by N-dealkylation, to form norbuprenorphine (N-dealkylbuprenorphine); buprenorphine and norbuprenorphine also undergo conjugation with glucuronic acid. Like the metabolites of other opioid agonists, norbuprenorphine may have weak analgesic activity; however, studies to determine the analgesic activity of the metabolites of buprenorphine have not been performed. Buprenorphine and its metabolites are excreted principally in feces via biliary elimination and also in urine. Buprenorphine is excreted in feces mainly as unchanged drug; small amounts of norbuprenorphine are also excreted in feces. The drug and its metabolites are believed to undergo enterohepatic circulation. Norbuprenorphine appears to be excreted principally in urine at a slower rate than the parent drug. Total plasma clearance of buprenorphine reportedly is approximately 1.28 l/minute in conscious postoperative patients. Limited data indicate that there is considerable interindividual variability in buprenorphine pharmacokinetics in children; however, clearance of the drug appears to be increased in children (e.g., those 5 to 7 years of age) compared with that in adults. Optimal dosing interval of buprenorphine may have to be decreased in pediatric patients.

Achieving effective analgesic plasma opioid concentrations in patients is very complicated and involves a host of considerations, including the inherent chemical and physical properties of the opioid itself. Further considerations include in-vivo metabolism, individual patient response and tolerance. Generally, however, there is a "minimally effective analgesic concentration" (MEAC) in plasma for a particular opioid below which no analgesia is provided. There is relationship between plasma opioid levels and analgesia. Higher plasma levels are generally associated with greater pain relief, and (possibly) greater incidence and severity of side effects.

In preferred embodiments of the present invention where the patient(s) is being treated for moderate to severe pain, the buprenorphine is administered in a manner such that the following mean plasma concentrations are achieved over a 72 hour dosing interval: a mean plasma concentration from about 0.3 to about 113 pg/ml at about 6 hours after initiation of the dosing interval; a mean plasma concentration from about 3 to about 296 pg/ml at about 12 hours after initiation of the dosing interval; a mean plasma concentration from about 7 to about 644 pg/ml at about 24 hours after initiation of the dosing interval; a mean plasma concentration from about 13 to about 753 pg/ml at about 36 hours after initiation of the dosing interval; a mean plasma concentration from about 16 to about 984 pg/ml at about 48 hours after initiation of the dosing interval; a mean plasma concentration from about 20 to about 984 pg/ml at about 60 hours after initiation of the dosing interval; a mean plasma concentration from about 21 to about 1052 pg/ml at about 72 hours after initiation of the dosing interval. Thereafter, the buprenorphine is administered in a manner such that the mean plasma concentrations are maintained from about 19 to about 1052 pg/ml over at least the next 48 hours. In further preferred embodiments, this method further comprises maintaining the dosing of buprenorphine during the at least next 48 hours in accordance with zero order kinetics. Preferably, the mean plasma concentrations are maintained after the 72 hour dosing inteval as follows: a mean plasma concentration from about 23 to about 1052 pg/ml at about 96 hours after initiation of the dosing interval; a mean plasma concentration from about 23 to about 1052 pg/ml at about 120 hours after initiation of the dosing interval; a mean plasma concentration from about 22 to about 970 pg/ml at about 144 hours after initiation of the dosing interval; and a mean plasma concentration from about 19 to about 841 pg/ml at about 168 hours after initiation of the dosing interval (for a seven day dosing interval). In this embodiment where a transde rmal delivery system is used, a mean relative release rate from about 3 ug/hr to about 86 ug/hr is preferably maintained from the initiation of the dosing interval until about 72 hours after the initiation of the dosing interval; and a mean relative release rate is preferably maintained from about 0.3 ug/hr to about 9 ug/hr from about 72 hours after the initiation of the dosing interval until the end of the dosing interval.

Preferably, the administration of buprenorphine is accomplished via a mode selected from the group consisting of transdermally, continuous infusion, and a mixture of transdermally and continuous infusion. Most preferably, the administration is accomplished by applying a transdermal delivery system to the skin of a patient, and maintaining said transdermal delivery system in contact with the patient's skin for at least 5 days.

In a further preferred embodiment of the invention, buprenorphine is administered to human patients in a manner such that the following mean plasma concentrations are achieved over a 72 hour dosing interval: a mean plasma concentration from about 1 to about 28 pg/ml at about 6 hours after initiation of the dosing interval; a mean plasma concentration from about 14 to about 74 pg/ml at about 12 hours after initiation of the dosing interval; a mean plasma concentration from about 30 to about 161 pg/ml at about 24 hours after initiation of the dosing interval; a mean plasma concentration from about 51 to about 188 pg/ml at about 36 hours after initiation of the dosing interval; a mean plasma concentration from about 62 to about 246 pg/ml at about 48 hours after initiation of the dosing interval; a mean plasma concentration from about 79 to about 246 pg/ml at about 60 hours after initiation of the dosing interval; a mean plasma concentration from about 85 to about 263 pg/ml at about 72 hours after initiation of the dosing interval. Thereafter, buprenorphine is administered in a manner such that the mean plasma concentrations are maintained from about 77 to about 263 pg/ml over at least the next 48 hours. Preferably, the plasma concentrations are maintained after the 72 hour dosing interval as follows: a mean plasma concentration from about 92 to about 263 g/ml at about 96 hours after initiation of the dosing interval; a mean plasma concentration from about 94 to about 263 pg/ml at about 120 hours after initiation of the dosing interval; a mean plasma concentration from about 86 to about 243 pg/ml at about 144 hours after initiation of the dosing interval; and a mean plasma concentration from about 77 to about 210 pg/ml at about 168 hours after initiation of the dosing interval (for a seven day dosing interval). In this embodiment wherein a transdermal delivery system is used, it is prefered that a mean relative release rate of from about 13 ug/hr to about 21 ug/hr is maintained from the initiation of the dosing interval until about 72 hours after the initiation of the dosing interval; and that a mean relative release rate of about 1 ug/hr to about 2 ug/hr from about 72 hours after the initiation of the dosing interval until the end of the dosing interval is maintained (e.g., about 168 hours after initiation for a seven-day dosing interval).

In a further preferred embodiment of the invention, buprenorphine is administered to human patients in a manner such that the following mean plasma concentrations are achieved over a 72 hour dosing interval: a mean plasma concentration from about 0.3 to about 7 pg/ml at about 6 hours after initiation of the dosing interval; a mean plasma concentration from about 4 to about 19 pg/ml at about 12 hours after initiation of the dosing interval; a mean plasma concentration from about 7 to about 40 pg/ml at about 24 hours after initiation of the dosing interval; a mean plasma concentration from about 13 to about 47 pg/ml at about 36 hours after initiation of the dosing interval; a mean plasma concentration from about 16 to about 62 pg/ml at about 48 hours after initiation of the dosing interval; a mean plasma concentration from about 21 to about 62 pg/ml at about 60 hours after in itiation of the dosing interval; a mean plasma concentration from about 20 to about 66 pg/ml at about 72 hours after initiation of the dosing interval. Thereafter, the buprenorphine is administered in a manner such that the mean plasma concentrations are maintained from about 19 to about 66 pg/ml over at least the next 48 hours. Preferably, the buprenorphine is administered in a manner such that the mean plasma concentrations are maintained as follows: a mean plasma concentration from about 23 to about 66 pg/ml at about 96 hours after initiation of the dosing interval; a mean plasma concentration from about 23 to about 66 pg/ml at about 120 hours after initiation of the dosing interval; a mean plasma concentration from about 22 to about 61 pg/ml at about 144 hours after initiation of the dosing interval; and a mean plasma concentration from about 19 to about 53 pg/ml at about 168 hours after initiation of the dosing interval (for a seven day dosing interval). In embodiments where a transdermal delivery system is used, a mean relative release rate is maintained from about 3 ug/hr to about 5 ug/hr from the initiation of the dosing interval until about 72 hours after the initiation of the dosing interval; and a mean relative release rate of about 0.3 ug/hr to about 0.6 ug/hr from about 72 hours after the initiation of the dosing interval until the end of the dosing interval (e.g., about 168 hours after initiation of a seven-day dosing interval).

In a further preferred embodiment of the invention, buprenorphine is administered to human patients in a manner such that the following mean plasma concentrations are achieved over a 72 hour dosing interval; a mean plasma concentration from about 0.7 to about 14 pg/ml at about 6 hours after initiation of the dosing interval; a mean plasma concentration from about 7 to about 37 pg/ml at about 12 hours after initiation of the dosing interval; a mean plasma concentration from about 15 to about 80 pg/ml at about 24 hours after initiation of the dosing interval; a mean plasma concentration from about 25 to about 94 pg/ml at about 36 hours after initiation of the dosing interval; a mean plasma concentration from about 31 to about 123 pg/ml at about 48 hours after initiation of the dosing interval; a mean plasma concentration from about 40 to about 123 pg/ml at about 60 hours after initiation of the dosing interval; a mean plasma concentration from about 42 to about 132 pg/ml at about 72 hours after initiation of the dosing interval. Thereafter, the buprenorphine is administered in a manner such that the mean plasma concentrations are maintained from about 38 to about 132 pg/ml over at least the next 48 hours. Preferably, the buprenorphine is fiirther administered in a manner such that the mean plasma concentrations are maintained as follows: a mean plasma concentration from about 46 to about 132 pg/ml at about 96 hours after initiation of the dosing interval; a mean plasma concentration from about 47 to about 132 pg/ml at about 120 hours after initiation of the dosing interval; a mean plasma concentration from about 43 to about 121 pg/ml at about 144 hours after initiation of the dosing interval; and a mean plasma concentration from about 38 to about 105 pg/ml at about 168 hours after initiation of the dosing interval (for a seven day dosing interval). In embodiments where a transdermal delivery system is used, a mean relative release rate from about 6 ug/hr to about 11 ug/hr is maintained from the initiation of the dosing interval until about 72 hours after the initiation of the dosing interval; and a mean relative release rate of about 0.7 ug/hr to about 1 ug/hr is maintained from about 72 hours after the initiation of the dosing interval until the end of the dosing interval (e.g., about 168 hours after initiation of a seven day dosing interval).

In a further preferred embodiment of the invention, buprenorphine is administered to human patients in a maner such that the following mean plasma concentrations are achieved over a 72 hour dosing interval: a mean plasma concentration from about 3 to about 57 pg/ml at about 6 hours after initiation of the dosing interval; a mean plasma concentration from about 28 to about 148 pg/ml at about 12 hours after initiation of the dosing interval; a mean plasma concentration from about 59 to about 322 pg/ml at about 24 hours after initiation of the dosing interval; a mean plasma concentration from about 102 to about 377 pg/ml at about 36 hours after initiation of the dosing interval; a mean plasma concentration from about 124 to about 492 pg/ml at about 48 hours after initiation of the dosing interval; a mean plasma concentration from about 159 to about 492 ml at about 60 hours; after initiation of the dosing interval; a mean plasma concentration from about 169 to about 526 pg/ml at about 72 hours after initiation of the dosing interval. Thereafter, the buprenorphine is administered in a manner such that the mean plasma concentrations are maintained from about 153 to about 526 pg/ml over at least the next 48 hours. Preferably, the buprenorphine is administered in a manner such that the mean plasma concentrations are maintained as follows: a mean plasma concentration from about 184 to about 526 pg/ml at about 96 hours after initiation of the dosing interval; a mean plasma concentration from about 187 to about 526 pg/ml at about 120 hours after initiation of the dosing interval; a mean plasma concentration from about 173 to about 485 pg/ml at about 144 hours after initiation of the dosing interval; a mean plasma concentration from about 153 to about 420 pg/ml at about 168 hours after initiation of the dosing interval (for a seven day dosing interval). In embodiments where a transdermal delivery system is used, a mean relative release rate from about 26 ug/hr to about 43 ug/hr is maintained from the initiation of the dosing interval until about 72 hours after the initiation of the dosing interval; and a mean relative release rate of about 2 ug/hr to about 4 ug/hr is maintained from about 72 hours after the initiation of the dosing interval until the end of the dosing interval (e.g., about 168 hours after initiation of a seven-day dosing interval).

In a further preferred embodiment of the invention, buprenorphine is administered to human patients in a manner such that the following mean plasma concentrations are achieved over a 72 hour dosing interval: a mean plasma concentration from about 4 to about 85 pg/ml at about 6 hours after initiation of the dosing interval; a mean plasma concentration from about 42 to about 222 pg/ml at about 12 hours after initiation of the dosing interval; a mean plasma concentration from about 89 to about 483 pg/ml at about 24 hours after initiation of the dosing interval; a mean plasma concentration from about 152 to about 565 pg/ml at about 36 hours after initiation of the dosing interval; a mean plasma concentration from about 186 to about 738 pg/ml at about 48 hours after initiation of the dosing interval; a mean plasma concentration from about 238 to about 738 pg/ml at 60 hours after initiation of the dosing interval; a mean plasma concentration from about 254 to about 789 pg/ml at about 72 hours after initiation of the dosing interval. Thereafter; the buprenorphine is administered in a manner such that the mean plasma concentrations are maintained from about 230 to about 789 pg/ml over at least the next 48 hours. Preferably, the buprenorphine is administered in a manner such that the mean plasma concentrations are maintained as follows: a mean plasma concentration from about 276 to about 789 pg/ml at about 96 hours after initiation of the dosing interval; a mean plasma concentration from about 281 to about 789 pg/ml at about 120 hours after initiation of the dosing interval; a mean plasma concentration from about 259 to about 727 pg/ml at about 144 hours after initiation of the dosing interval; a mean plasma concentration from about 230 to about 630 pg/ml at about 168 hours a after initiation of the dosing interval (for a seven day dosing interval). In embodiments where a transdermal delivery system is used, a mean relative release rate of from about 38 ug/hr to about 64 ug/hr is maintained from the initiation of the dosing interval until about 72 hours after the initiation of the dosing interval; and a mean relative release rate of about 4 ug/hr to about 7 ug/hr is maintained from about 72 hours after the initiation of the dosing interval until the end of the dosing interval (e.g., about 168 hours after the initiation of a seven-day dosing interval).

In a further preferred embodiment of the invention, buprenorphine is administered to human patients in a manner such that the following mean plasma concentrations are achieved over a 72 hour dosing interval: a mean plasma concentration from about 5 to about 113 pg/ml at about 6 hours after initiation of the dosing interval; a mean plasma concentration from about 55 to about 296 pg/ml at about 12 hours after initiation of the dosing interval; a mean plasma concentration from about 118 to about 644 pg/ml at about 24 hours after initiation of the dosing interval; a mean plasma concentration from about 203 to about 753 pg/ml at about 36 hours after initiation of the dosing interval; a mean plasma concentration from about 247 to about 984 pg/ml at about 48 hours after initiation of the dosing interval; a mean plasma concentration from about 317 to about 984 pg/ml at about 60 hours after initiation of the dosing interval; a mean plasma concentration from about 339 to about 1052 pg/ml at about 72 hours after initiation of the dosing interval. Thereafter, the buprenorphine is administered in a manner such that the mean plasma concentrations are maintained from about 306 to about 1052 pg/ml over at least the next 48 hours. Preferably, the buprenorphine is administered in a manner such that the mean plasma concentrations are maintained as follows: a mean plasma concentration from about 369 to about 1052 pg/ml at about 96 hours after in itiation of the dosing interval; a mean plasma concentration from about 374 to about 1052 pg/ml at about 120 hours after initiation of the dosing interval; a mean plasma concentration from about 346 to about 970 pg/mil at about 144 hours after initiation of the dosing interval; a mean plasma concentration from about 306 to about 841 pg/ml at about 168 hours after initiation of the dosing interval (for a seven day dosing interval). In embodiments where a transdermal delivery system is used, a mean relative release rate of from about 51 ug/hr to about 86 ug/hr is maintained from the initiation of the dosing interval until about 72 hours after the initiation of the, e.g., dosing interval; and a mean relative release rate of about 5 ug/hr to about 9 ug/hr is maintained from about 72 hours after the initiation of the dosing interval until the end of the dosing interval, e.g., about 168 hours after the initiation of a seven-day dosing interval (e.g., about 168 hours after the initiation of a seven-day dosing internal).

In further embodiments of the invention, the method comprises the administration of buprenorphine transdermally to human patients according to very different relative release rates for the first 3 day portion of the dosing interval (indicative of substantially first order release), and the additional at least 2 day long portion of the dosing interval (substantially zero order release) such that mean relative release rates are achieved over the dosing interval as follows: a mean relative release rate of from about 3 ug/hr to about 86 ug/hr from the initiation of the dosing interval until about 72 hours after the initiation of the dosing interval; and a mean relative release rate of about 0.3 ug/hr to about 9 ug/hr from about 72 hours after the initiation of the dosing interval until the end of the dosing interval (e.g., about 168 hours after the initiation of a seven-day dosing interval).

In one preferred embodiment, the mean relative release rates achieved over the dosing interval are as follows: a mean relative release rate of from about 3 ug/hr to about 5 ug/hr from the initiation of the dosing interval until about 72 hours after the initiation of the dosing interval; and a mean relative release rate of about 0.3 ug/hr to about 0.6 ug/hr from about 72 hours after the initiation of the dosing interval until the end of the dosing interval (e.g., about 168 hours after initiation of a seven-day dosing interval).

In another preferred embodiment, the mean relative release rates achieved over the dosing interval are as follows: a mean relative release rate of from about 6 ug/hr to about 11 ug/hr from the initiation of the dosing interval until about 72 hours after the initiation of dosing interval; and a mean relative release rate of about 0.7 ug/hr to about 1 ug/hr from about 72 hours after the initiation of the dosing interval until the end of the dosing interval (e.g., about 168 hours after initiation of a seven-day dosing interval).

In another preferred embodiment, the mean relative release rates achieved over the dosing interval are as follows: a mean relative release rate of from about 13 ug/hr to about 21 ug/hr from the initiation of the dosing interval until about 72 hours after the initiation of the dosing interval; and a mean relative release rate of about 1 ug/hr to about 2 ug/hr from about 72 hours after the initiation of the dosing interval until the end of the dosing interval (e.g., about 168 hours after initiation of a seven-day dosing interval).

In yet another preferred embodiment, the mean relative release rates achieved over the dosing interval are as follows: a mean relative release rate of from about 26 ug/hr to about 43 ug/hr from the initiation of the dosing interval until about 72 hours after the initiation of the dosing interval; and a mean relative release rate of about 3 ug/hr to about 4 ug/hr from about 72 hours after the initiation of the dosing interval until the end of the dosing interval (e.g., about 168 hours after the initiation of a seven-day dosing interval).

In yet a further preferred embodiment, the mean relative release rates achieved over the dosing interval are as follows: a mean relative release rate of from about 39 ug/hr to about 64 ug/hr from the initiation of the dosing interval until about 72 hours after the initiation of the dosing interval; and a mean relative release rate of about 4 ug/hr to about 7 ug/hr from about 72 hours after the initiation of the dosing interval until the end of the dosing interval (e.g., about 168 hours after the initiation of a seven-day dosing interval).

In yet a further preferred embodiment, the mean relative release rates achieved over the dosing interval are as follows: a mean relative release rate of from about 51 ug/hr to about 86 ug/hr from the initiation of the dosing interval until about 72 hours after the initiation of the dosing interval; and a mean relative release rate of about 5 ug/hr to about 9 ug/hr from about 72 hours after the initiation of the dosing interval until the end of the dosing interval, e.g., about 168 hours after the initiation of the dosing interval.

The method of the present invention may be accomplished by any mode of administration useful for buprenorphine known to those slilled in the art. However, certain modes of administration are more practical than others. Preferably, the mode of administration is via continuous infusion, through the oral mucosa, or most preferably, transdermally.

In embodiments of the invention where the plasma concentrations described herein are accomplished intravenous infusion, the pattern of plasma concentrations seen through time in this invention can be achieved by using the injectable, parenteral form of, e.g., buprenorphine hydrochloride suitably diluted in an intravenous infusion solution. The infusion rate would be controlled by a programmable infusion pump, to provide the desired plasma profile.

In preferred embodiments of the invention, the mode of administration of the buprenorphine is transdermal. Transdermal delivery of active agents is measured in terms of "relative release rate" or "flux", i.e., the rate of penetration of the active agent through the skin of an individual. Skin flux may be generally determined from the following equation:

$$dM/dt = J = P*C$$

where J is the skin flux, P is the permeability coefficient and C is the concentration gradient across the membrane, assumed to be the same as the donor concentration. M represents the cumulative amount of drug entering the blood stream. The variables dM and dt represent the change in cumulative amount of drug entering the blood stream and change in time, respectively.

It is well understood in the art of transdermal delivery systems that in order to maintain a desired flux rate for a desired dosing period, it is necessary to include an overage of active agent in the transdermal delivery system in an amount that is substantially greater than the amount to be delivered to the patient over the desired time period. For example, to maintain the desired flux rate for a three day time period, it is considered necessary to include much greater than 100% of a three day dose of an active agent in a transdermal delivery system. This overage is necessary for creating a concentration gradient by means of which the active agent migrates through the layers of the transdermal delivery system to the desired site on a patient's skin. The remainder of the active agent remains in the transdermal delivery system. It is only the portion of active agent that exits the transdermal delivery system that becomes available for absorption into the skin. The total amount of active agent absorbed into the patient's blood stream is less than the total amount available. The amount of overage to be included in a transdermal delivery system is dependent on these and other factors known to the skilled artisan.

Surprisingly, it has been found that it is possible to treat pain according to the present invention by providing a transdermal delivery system containing a sufficient amount of opioid, e.g. buprenorphine, to provide a desired relative release rate for up to 3 days, and after single administration (application) of the transdermal dosage form, leaving the dosage form on the skin for approximately a 5 to 8 day time period, thereby resulting in the flux being maintained over the prolonged period and effective blood plasma levels and pain management being maintained over the prolonged period. Preferably, the desired flux is maintained at least about 5, preferably at least about 8 days after application of the transdermal delivery system. If the transdermal delivery system is removed 3 days after its administration, no analgesia is present a short time after removal. Surprisingly however, if the same transdermal delivery system is maintained in contact with the skin for an about 5 to about 8 day period, analgesia is maintained over the prolonged period of contact, but the patient continues to experience analgesia. In other words, inclusion of the aforementioned overage of buprenorphine provides analgesia for at least about twice the expected 3 day dosing interval.

Any type of transdermal delivery system may be used in accordance with the methods of the present invention so long as the desired pharmacokinetic and pharmacodynamic response(s) are attained over at least 3 day s, e.g., from about 5 to about 8 days. Preferable transdermal delivery systems include e.g., transdermal patches, transdermal plasters, transdermal discs, iontophoretic transdermal devices and the like.

Transdermal dosage forms used in accordance with the invention preferably include a backing layer made of pharmaceutically acceptable material which is impermeable to the buprenorphine. The backing layer preferably serves as a protective cover for the active agent, e.g. buprenorphine and may also provide a support function. Examples of materials suitable for making the backing layer are films of high and low density polyethylene, polypropylene, polyvinylchloride, polyurethane, polyesters such as poly(ethylene phthalate), metal foils, metal foil laminates of such suitable polymer films, textile fabrics, if the components of the reservoir cannot penetrate the fabric due to their physical properties and the like. Preferably, the materials used for the backing layer are laminates of such polymer films with a metal foil such as aluminum foil. The backing layer can be any appropriate thickness which will provide the desired protective and support functions. A suitable thickness will be from about 10 to about 200 microns. Desirable materials and thickness will be apparent to the skilled artisan.

In certain preferred embodiments, the transdermal dosage forms used in accordance with the invention contain a polymer matrix layer. Generally, the polymers used to form the biologically acceptable polymer matrix are those capable of forming thin walls or coatings through which pharmaceuticals can pass at a controlled rate. A non-limiting list of exemplary materials for inclusion in the polymer matrix includes polyethylene, polypropylene, ethylene/propylene copolymers, ethylene/ethylacrylate copolymers, ethylenevinyl acetate copolyrners, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof.

Preferred materials for inclusion in the polymer matrix layer are silicone elastomers of the general polydimethylsiloxane structures, (e.g., silicone polymers). Preferred silicone polymers cross-link and are pharmaceutically acceptable. Other preferred materials for inclusion in the polymer matrix layer include: silicone polymers that are crosslinkable copolymers having dimethyl and/or dimethylvinyl siloxane units which can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

The polymer matrix layer may optionally include a pharmaceutically acceptable cross-linking agent. Suitable crosslinking agents include, e.g., tetrapropoxy silane.

Preferred transdermal delivery systems used in accordance with the methods of the present invention include an adhesive layer to affix the dosage form to the skin of the patient for a desired period of administration, e.g., about 5 to about 8 days. If the adhesive layer of the dosage form fails to provide adhesion for the desired period of time, it is possible to maintain contact between the dosage form with the skin by, for instance, affixing the dosage form to the skin of the patient with an adhesive tape, e.g, surgical tape. It is not critical for purposes of the present invention whether adhesion of the dosage form to the skin of the patient is achieved solely by the adhesive layer of the dosage form or in connection with a peripheral adhesive source, such as surgical tape, provided that the dosage form is adhered to the patient's skin for the requisite administration period.

The adhesive layer preferably includes using any adhesive known in the art that is pharmaceutically compatible with the dosage form and preferably hypoallergenic, such as polyacrylic adhesive polymers, acrylate copolymers (e.g., polyacrylate) and polyisobutylene adhesive polymers. In other preferred embodiments of the invention, the adhesive is a pressure-sensitive contact adhesive, which is preferably hypoallergenic.

The transdermal dosage forms which can be used in accordance with the present invention may optionally include a permeation enhancing agent. Permeation enhancing agents are compounds which promote penetration and/or absorption of the buprenorphine into the blood stream of the patient. A non-limiting list of permeation enhancing agents includes polyethylene glycols, surfactants, and the like.

Alternatively, permeation of buprenorphine may be enhanced by occlusion of the dosage form after application to the desired site on the patient with, e.g. an occlusive bandage. Permeation may also be enhanced by removing hair from the application site by, e.g. clipping, shaving or use of a depilatory agent. Another permeation enhancer is heat. It is thought that heat enhancement can be induced by, among other things, using a radiating heat form, such as an infrared lamp, onto the application site after application of the transdermal dosage form. Other means of enhancing permeation of buprenorphine such as the use of iontophoretic means are also contemplated to be within the scope of the present invention.

A preferred transdernal dosage form which may be used in accordance with the present invention includes a non-permeable backing layer made, for example, of polyester, an adhesive layer made, for example of a polyacrylate; and a matrix containing the buprenorphine and other desirable pharm aceutical aids such as softeners, permeability enhancers, viscosity agents and the like.

The active agent may be included in the device in a drug reservoir, drug matrix or drug/adhesive layer. Preferably, the active agent is buprenorphine or a pharmaceutically acceptable salt thereof.

Certain preferred transdermal delivery systems also include a softening agent. Suitable softening agents include higher alcohols such as dodecanol, undecanol, octanol, esters of carboxylic acids, wheren the alcohol component may also be a polyethoxylated alcohol, diesters of dicarboxyric acids, such as di-n-butyladiapate, and triglycerides particularly medium-chain triglycerides of the caprylic/capric acids or coconut oil, have proved to be particularly suitable. Further examples of suitable softeners are multivalent alcohols, for example, levulinic acid, coeprylic acids glycerol and 1,2-propanediol which can also be etherified by polyethylene glycols.

A buprenorphine solvent may also be included in the transdermal delivery systems of the present invention. Preferably, the solvents dissolve the buprenorphine to a sufficient extent thereby avoiding complete salt formation. A non-limiting list of suitable solvents include those with at least one acidic group. Particularly suitable are monoesters of dicarboxylic acids such as monomethylglutarate and monomethyladipate.

Other pharmaceutically acceptable compounds which may be included in the reservoir or matrix include: solvents, for example alcohols such as isopropanol; permeation enhancing agents such as those described above; and viscosity agents, such as cellulose derivatives, natural or synthetic gums, such as guar gum, and the like.

In preferred embodiments, the transdermal dosage form includes a removable protective layer. The removable protective layer is removed prior to application, and consists of the materials used for the production of the backing layer described above provided that they are rendered removable, for example. by a silicone treatment. Other removable protective layers, for example, are polyletra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

The composition of the transdermal dosage forms used in accordance with the invention and the type of device used are not considered critical to the method of the invention, provided that the device delivers the active agent, e.g. buprenorphine, for the desired time period and at the desired flux rate and/or the desired delivery rate of the transdermal dosage form.

Certain preferred tranderrmal dosage forms for use in accordance with the present invention are described in U.S. Pat. No. 5,240,711 (Hille, el. al.; assigned to LTS Lohmann Therapie-Systeme GmbH & Co.), hereby incorporated by reference. Such buprenorphine transdermal delivery systems may be a laminated composite having an impermeable backing layer containing buprenorphine, and optionally, a permeation enhancer combined with a pressure-sensitive adhesive. A preferred transdermal dosage form in accordance with the '711 patent includes: (i) a polyester backing layer which is impermeable to buprenorphine; (ii) a polyacrylate adhesive layer; (iii) a separating polyester layer; and (iv) a matrix containing buprenorphine, a solvent for the buprenorphine, a softener and a polyacrylate adhesive. The buprenorphine solvent may or may not be present in the final formulation. The transdermal delivery device described therein includes a backing layer which is impermeable to the active substance, a pressure-sensitive adhesive reservoir layer and optionally, a removable protective layer. Preferably, the reservoir layer includes about 10 to about 95%-wt polymeric material, about 0.1 to about 40%-wt softener, about 0.1 to about 30%-wt buprenorphine. A solvent for the buprenorphine base or pharmaceutically acceptable salt thereof may be included as about 0.1 to about 30%-wt.

In a preferred embodiment, the transdermal delivery system is prepared in accordance with Example 1 appended hereto. In this example, the transdermal delivery system was prepared in accordance with the disclosure of International Patent Application No. WO 96/19975 (Hille, et. al.; assigned to LTS Lohmann Therapie-Systeme GMBH), hereby incorporated by reference. In this device, the buprenorphine transdermal delivery device contains resorption-promoting auxiliary substances. The resorption-promoting auxiliary substance forms an undercooled mass. The delivery system contains 10% buprenorphine base, 10–15% acid (such as levulinic acid), about 10% softener (such as oleyoleate); 55–70% polyacrylate; and 0–10% polyvinylpyrollidone (PVP).

In embodiments of the present invention wherein the buprenorphine plasma concentrations described herein are achieved via the use of a transdermal delivery device prepared in accordance with WO 96/19975, it is contemplated for example that the nominal delivery rate of buprenorphine from such patches will be, e.g., from about 12.5 to about 100 ug/hr. In certain preferred embodiments, in order to achieve a nominal delivery rate of 12.5 ug/hr, the total of buprenorphine included in the transdermal patch is about 5 mg, the active surface area is about 6.25 $cm^2$ and the patch size may be, e.g., about 19.4 $cm^2$. In certain preferred embodiments, in order to achieve a nominal delivery rate of 25 ug/hr, the total of buprenorphine included in the transdermal patch is about 10 mg, the active surface area is about 12.5 $cm^2$ and the patch size may be, e.g., about 30.6 $cm^2$. In certain preferred embodiments, in order to achieve a nominal delivery rate of 50 ug/hr, the total of buprenorphine included in the transdermal patch is about 20 mg, the active surface area is about 25 $cm^2$ and the patch size may be, e.g., about 51.8 $cm^2$. In certain preferred embodiments, in order to achieve a nominal delivery rate of 75 ug/hr, the total of buprenorphine included in the transdermal patch is about 30 mg, the active surface area is about 37.5 $cm^2$ and the patch size may be, e.g., about 69.8 $cm^2$. In certain preferred embodiments, in order to achieve a nominal delivery rate of 100 ug/hr, the total of buprenorphine included in the transdermal patch is about 40 mg, the active surface area is about 50 $cm^2$ and the patch size may be, e.g., about 87.8 $cm^2$.

In accordance with a method of the invention, the above-described transdermal delivery system has been designed to be adhered to the patient for only three days and is expected to release analgetically effective doses of buprenorphine for only about 3 days. Instead, in accordance with the present invention, the transdermal delivery device is maintained in contact with the skin of the patient for a much longer time period, e.g., from about 5 to about 8 days, without any change in the formulation of the transdermal device itself. It has surprisingly been found that analgesia is maintained for this extended period of time (the time beyond the useful life designed for the transdermal formulation).

In other embodiments, the buprenorphine transdermal delivery system may be a plaster such as that described in U.S. Pat. No. 5,225,199 to Hidaka et al., hereby incorporated by reference. Such plasters include a film layer including a polyester film of about 0.5 to about 4.9 $\mu$m thickness, about 8 to about 85 g/mm strength, respectively in the two directions intersecting substantially at right angles, about 30 to about 150% elongation, in the two directions intersecting substantially at right angles and an elongation ratio of A to B of about 1.0 to about 5.0, wherein A and B represent data in two directions intersecting at right angles, and A is greater than B and wherein said polyester film includes about 0.01 to about 1.0% by weight, based on the total weight of the polyester film, of solid fine particles in which the average particle size is about 0.001 to about 3.0 $\mu$m and an adhesive layer which is composed of an adhesive containing transdermally absorbable drugs; wherein the adhesive layer is laminated on said film layer over the surface in about 2 to about 60 $\mu$m thickness. The average particle size is substantially not more than 1.5 times the thickness of the polyester film.

The transdermal delivery system used in the present invention may also be prepared in accordance with U.S. Pat. No. 5,069,909 (Sharma et al.), hereby incorporated by reference. This patent describes a laminated composite for administering buprenorphine transdermally to treat pain. The composite includes an impermeable backing layer providing a protective covering for the composite which may be made from an alastomeric polymer such as polyurethane, polyether amide, or copolyester and may be about 15–250 microns in thickness. The composite further includes a reservoir lamina composed of buprenorphine (base or HCl) in an amount of 1–12% by weight and a pressure-sensitive adhesive, e.g., polyisobutylene, or a silicone adhesive such as silastic, or an acrylate adhesive, and 2–35% permeation enhancer (comprising propylene glycol monolaurate in combination with capric acid or oleic acid). The amounts of buprenorphine and permeation enhancer are sufficient to cause the buprenorphine to pass through the skin at a rate of about 1 to 100 $\mu g/cm^2/hr$.

The transdermal delivery system used in the present invention may also be prepared in accordance with U.S. Pat. No. 4,806,341 (Chien et al.), hereby incorporated by reference. This patent describes a transdermal morphinan narcotic analgesic or antagonist (including buprenorphine) pharmaceutical polymer matrix dosage unit having a backing layer which is substantially impervious to the buprenorphine, and a polymer matrix disc layer which is adhered to the backing layer and which has microdispersed therein effective dosage amounts of the buprenorphine. The polymer matrix may be a silicon polymer or copolymer, such as methyl silicone polymer or copolymer, or methylvinyl silicone polymer or copolymer. The polymer matrix layer preferably has dispersed therein a skin permeation enhancing agent such as isopropyl myristate, azone, or a combination of ethyl caprylate and capryl alcohol.

The transdermal delivery system used in the present invention may also be that described in U.S. Patent No. 5,026,556 (Drust et al.), hereby incorporated by reference. Therein, compositions for the transdermal delivery of buprenorphine comprise buprenorphine in a carrier of a polar solvent material selected from the group consisting of $C_3$–$C_4$ diols, $C_3$–$C_6$ triols, and mixtures thereof, and a polar lipid material selected from the group consisting of fatty alcohol esters, fatty acid esters, and mixtures thereof; wherein the polar solvent material and the lipid material are present in a weight ratio of solvent material:lipid material of from 60:40 to about 99:1.

The transdermal delivery system used in the present invention may also be that described in U.S. Pat. No. 4,588,580 (Gale, et. al.), hereby incorporated by reference. That system comprises a reservoir for the drug having a skin proximal, material releasing surface area in the range of about 5–100 $cm^2$ and containing between 0.1 and 50% by weight of a skin permeable form of the buprenorphine. The reservoir contains an aqueous gel comprising up to about 47–95% ethanol, 1–10% gelling agent, 0.1–10% buprenorphine, and release rate controlling means disposed in the flow path of the drug to the skin which limits the flux of the buprenorphine from the system through the skin. The release rate controlling means is more permeable to the buprenorphine than to the ethanol, and may be for example low density polyethylene (LDPE), ehtylene-vinyl acetate (EVA) copolymers, heat sealable polyesters, and elastomeric polyester block copolymers, such as HYTREL® from DuPont. This system is said to be capable of providing an administration rate of about 10–300 µg/hr. It is contemplated that each of the transdermal delivery systems described herein (other than the system exemplified in Example 1 appended hereto) would require minor manipulation in order to achieve the methods of the invention. Such modifications are within the abilities of one skilled in the art of formulating such transdermal delivery systems.

The present invention may also be accomplished via the use of a sustained oral mucosal delivery system. Such a system is described by McQuinn, R. L. et al., "Sustained Oral Mucosal Delivery in Human Volunteers *J. Controlled Release;* (34) 1995 (243–250). Therein, oral mucosal patches were prepared by homogeneously mixing buprenorphine free base (8%), Carbopol 934 (52%), polyisobutylene (35%) and polyisoprene (5%, w/w) via a two-roll mill and then compressing the mixture to the appropriate thickness. A membrane backing (ethylcellulose) was applied to one side of the compressed material and then circular disks (0.5 cm$^2$) were punched from the material. The backing was included in order to retard drug release from one side of the disk and to prohibit adhesion to opposing side tissues. Each soft, flexible disk was approximately 0.6 mm thick and contained 2.9 mg buprenorphine. These patches were worn by the subjects for 12 hours. Gum and lip application was tested, although adhesion at the gum site was considered superior. After the initial appearance of serum buprenorphine ($\geq$25 pg/ml), levels generally increased relatively rapidly and persisted until the patch was removed. After the patch was removed, buprenorphine levels fell promptly and were at a relatively low (but measureable) level by 24 hours postdose. It was estimated that 0.42±0.18 mg were delivered via the gum treatment. From this discussion, it is apparent that an oral mucosal patch can be prepared which will provide plasma concentrations considered desirable according to the present invention.

A significantly higher incidence in side effects such as nausea, vomiting or drowsiness would normally be expected when high blood levels of opioid analgesics are administered. The present invention, by maintaining a lower blood level of drug over the 7 day dosing period while maintaining effective pain management, has a lower incidence of side effects. In comparison, a much higher plasma concentration is seen in patients over the same period of time when a new transdermal delivery device of the same strength is put on every three days, and therefore increased side effects are expected with each new 3 day transdermal application.

In general upon administration of an opioid analgesic, there is a lag time or "hysteresis", between the pharmacodynamic effects and the time course of opioid plasma concentration levels. Generally, peak plasma level concentrations are often attained prior to exhibition of the maximum pharmacotherapeutic or side effect response. It has been surprisingly discovered that the method according to the present invention provides a "reverse hysteresis", i.e. the rise in plasma concentrations follow the appearance and rise of certain of the pharmacodynamic events and side effects.

DETAILED DESCRIPTION OF PREFERRED EMBODIMENTS

The following examples illustrate various aspects of the present invention. They are not to be construed to limit the claims in any manner whatsoever.

EXAMPLE 1

A seven day pharmacolkinetic/pharmacodynamic study was conducted on 24 healthy human patients. The subjects were comprised of approximately an equal number of male and female subjects. In this study, the buprenorphine was administered via a transdermal patch which is described in WO 96/19975.

The transdermal patch is prepared in accordance with the disclosure of WO 96/19975 for Example 1 therein as follows:

1.139 g of a 47.83 w/% polyacrylate solution with a self-netting acrylate copolymers containing 2-ethylhexylacrylates, vinyl acetates, acrylic acid (dissolving agent:ethylacetate:heptan:iso-propanol:toluol:acetylacetonate in the ratio of 37:26:26:4:1), 100 g laevulinic acid, 150 g oleyloleate, 100 g polyvinylpyrollidone, 150 g ethanol, 200 g ethyl acetate and 100 g buprenorphine base are homogenized. The mixture is stirred for about 2 hours and then examined visually to determine if all solid substances have been dissolved. One has to control the evaporation loss by method of weighing back and makes up for the solvent with the help of ethylacetate, if necessary. Thereafter, the mixture is put onto. a 420 mm wide, transparent polyester foil, since the surface weight of the dried layer of paste is 80 g per m$^2$. The polyester foil which can be dissolved again with treatment of silicone serves as a protective layer. The solvent is removed by drying with heated air which is led over a moist lane. With this treatment of warmth not only do solvents evaporate but the the laevulinic acid melts as well. Thereafter, the sealing film is covered with a polyester foil 15 µab. A surface of about 16 cm$^2$ is cut with the help of the appropriate cutting tool, and the rims that have been left between the individual systems are removed.

The formulation utilized for Example 1 is substantially the same as that described in Example 3 of WO 96/19975, which is prepared in accordance with Example 1 and is stated therein to include 10% buprenorphine, 10% levulinic acid, 10% polyvinylpyrollidone, 10% oleyloeate, and 60% polyacrylate.

In order to achieve the nominal delivery rate of 25 ug/hr expected for the formulation of Example 1, the total of buprenorphine included in the transdermal patch is about 10 mg, the active surface area is about 12.5 cm$^2$ and the patch size may be, e.g., about 30.6 cm$^2$.

The dosing regimen was one (1) patch containing 10 mg buprenorphine base/patch reservoir applied to the subject's skin and maintained in contact with the skin for a time period of seven (7) days.

The adhesive patch with the medication being tested was placed on the right midaxillary line at the level of the 5th intercostal space at approximately 0800 hr on day 1. For patch application, the skin was washed with lukewarm soapy water, then rinsed with clear water and left to air dry. The skin was not rubbed while it was being washed. The application site was relatively hairless. Hair was not clipped or shaven. The patches were removed at approximately 0800 hr on day 8. Following patch removal, the patch site was not washed or rubbed until the last blood collection for that treatment period was over. Each patch was placed unfolded onto its release liner and the patch/release liner unit was placed back in the correct pouch, which was then sent to a bioanalytical laboratory for residual buprenorphine assay.

Blood sampling (10 ml at each time point) started on day 1, and continued thereafter at the following times: 1 hr (pre-dose) and at regular intervals thereafter during the 7 day dosing interval.

Patch site skin observations of the patch sites were performed by the investigator/staff rating the quality of the skin at the site of the actual medication reservoir of the patch at 0 hr (prior to patch placement) and 30 minutes after patch removal. The rating scale was as follows:

Erythema: 0=No visible redness; 1=Very slight redness (just perceptible); 2=Slight but well-defined redness; 3=Moderately intense redness; 4=Severe erythema (dark red discoloration of the skin).

Edema: 0=No visible reactions; 1=Very mild edema (just perceptible); 2=Mild edema (corners of the area are well defined due to noticeable swelling); 3=Moderate edema (up to 1 mm swelling in diameter); 4=Severe edema (more than 1 mm swelling in diameter, protruding over the edges of the patch).

The following pharmacokinetic parameters were estimated: $AUC_{(o\text{-}last)}$ (pg.hr/ml)—the area under the curve from time zero to the time of last non-zero plasma buprenorphine concentration, calculated by the linear trapezoidal method; $C_{max}$ (pg/ml)—maximum observed plasma buprenorphine concentration over the dosing interval; if $C_{max}$ occurs at more than one time point, $T_{max}$ is defined as the time point for the first $C_{max}$; residual=buprenorphine remaining in used patches (mg/patch).

A summary of the plasma buprenorphine concentrations (provided in picograms per milliliter, or pg/ml), is set forth in Table 1 below:

TABLE 1

| HOURS[1] | MEAN[2] | STD. DEV.[3] | CV %[4] |
|---|---|---|---|
| 6 | 1.76 | 6.20 | 352.77 |
| 12 | 18.47 | 26.00 | 140.78 |
| 18 | 39.45 | 36.16 | 91.67 |
| 24 | 58.94 | 44.66 | 75.76 |
| 30 | 67.69 | 48.78 | 72.06 |
| 36 | 82.44 | 53.02 | 64.32 |
| 42 | 107.61 | 65.43 | 60.81 |
| 48 | 104.69 | 60.69 | 57.97 |
| 54 | 105.81 | 66.68 | 63.02 |
| 60 | 112.93 | 63.02 | 55.81 |
| 66 | 129.25 | 64.37 | 49.80 |
| 72 | 130.55 | 64.16 | 49.14 |
| 78 | 122.83 | 54.97 | 44.75 |
| 84 | 129.03 | 51.50 | 39.92 |
| 90 | 139.50 | 68.26 | 48.93 |
| 96 | 146.70 | 62.76 | 42.78 |
| 102 | 130.19 | 57.68 | 44.31 |
| 108 | 135.49 | 67.72 | 49.98 |
| 114 | 150.24 | 71.69 | 47.72 |
| 120 | 136.22 | 63.62 | 46.70 |
| 126 | 130.25 | 57.77 | 44.35 |
| 132 | 124.78 | 52.82 | 42.34 |
| 138 | 138.55 | 58.34 | 42.11 |
| 144 | 115.23 | 48.30 | 41.92 |
| 150 | 116.30 | 49.04 | 42.16 |
| 156 | 120.07 | 50.88 | 42.38 |
| 162 | 117.66 | 52.71 | 44.80 |
| 168 | 102.00 | 49.92 | 48.94 |

[1] hours after administration of dose (e.g., application of patch)
[2] mean blood plasma concentration for the 24 test subjects (pg/ml)
[3] standard deviation of mean blood plasma concentrations
[4] coefficient of variation (%)

The mean plasma concentrations are further depicted in FIG. 1 (concentration pg/ml vs. time (days)). It is apparent from the pharmacokinetic results obtained with respect to Example 1 that the mean blood plasma concentrations rose steadily and peaked at about the 3-day time point during the dosing interval (e.g., about 72 hours after application of the patch), and thereafter surprisingly remained relatively steady throughout the remaining portion of the dosing interval (e.g., to about the 7-day time point, 168 hours after initiation of the dosing interval). Further, it is apparent from the buprenorphine plasma concentrations that first order kinetics were present during the first 72 hours of the dosing interval, and substantially zero order kinetics were present thereafter.

A summary of the pharmacokinetic parameters obtained for Example 1 are set forth in Table 2 below:

TABLE 2

|  | MEAN | STD. DEV. | GEOMETRIC MEAN | CV % |
|---|---|---|---|---|
| AUC (0–168 hrs) | 17740.68 | 7503.50 | 16263.88 | 42.30 |
| Cmax (pg/ml) | 184.80 | 68.84 | 171.78 | 37.25 |
| Tmax (hrs) | 110.50 | 26.48 |  | 23.96 |

Figure 2:
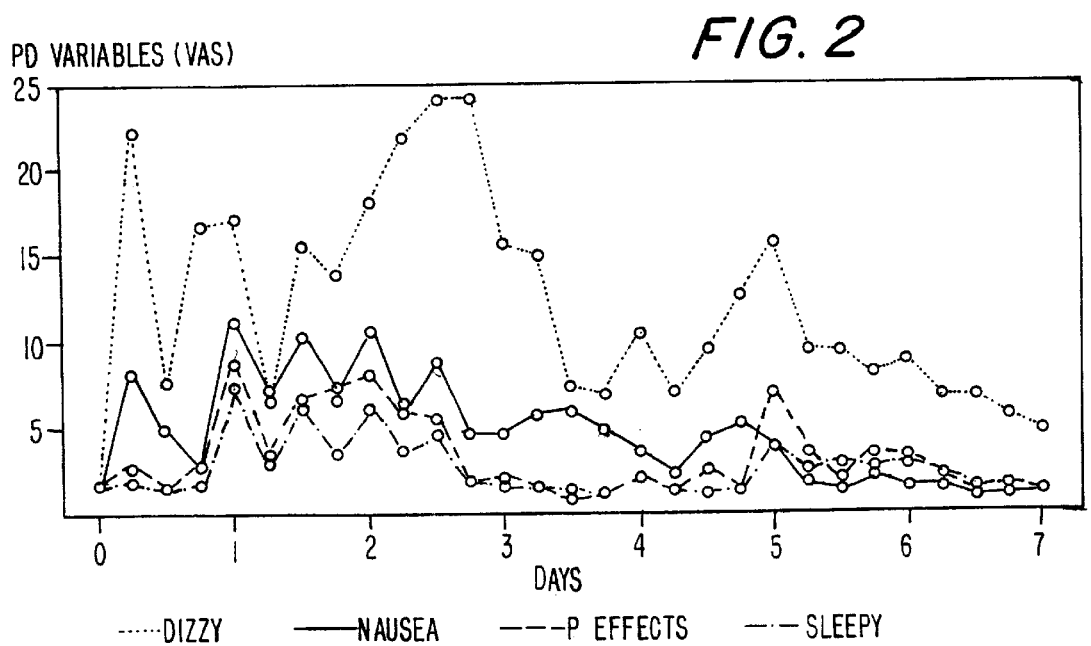
FIG. 2 is a graphical representation of pharmacodynamic variables versus time (days) for Example 1.

The following pharmacodynamic parameters were assessed 5 minutes prior to each blood collection by having each patient respond to several questions by placing a vertical mark at the appropriate spot on a 100 mm visual analog scale ("VAS") anchored on one end by "not at all" and on the other end by "an awful lot". The first question asked to the subjects was "Do you feel any effect of the drug?" After the patient marked his/her response on the VAS to this question, responses were obtained via the VAS as to whether the subjects had experienced (i) nausea, (ii) dizziness, and (iii) sleepiness. The results are set forth in Table 3. All pharmacodynamic parameters were sumrized and tabulated. Then a mixed (linear or nonlinear) effect was used to model the pharmacokinetic and pharmacodynamic relationships, The results concerning pharmacodynamic parameters (VAS) are set forth in FIG. 2.

TABLE 3

SUMMARY OF SEVERITY FOR THE MOST COMMONLY REPORTED
(>=10% OF SUBJECTS) ADVERSE EVENTS
(RELATED TO TREATMENT)
(N = 24)

|  | MILD | | MODERATE | | SEVERE | | TOTAL | |
|---|---|---|---|---|---|---|---|---|
|  | N | (%) | N | (%) | N | (%) | N | (%) |
| CONSTIPATION | 3 | 12.5 | 0 | 0.0 | 0 | 0.0 | 3 | 12.5 |
| DIZZINESS | 8 | 33.3 | 0 | 0.0 | 0 | 0.0 | 8 | 33.3 |
| HEADACHE | 7 | 29.2 | 0 | 0.0 | 0 | 0.0 | 7 | 29.2 |
| NAUSEA | 6 | 25.0 | 0 | 0.0 | 0 | 0.0 | 6 | 25.0 |
| RASH | 20 | 83.3 | 0 | 0.0 | 0 | 0.0 | 20 | 83.3 |
| SOMNOLENCE | 11 | 45.8 | 0 | 0.0 | 0 | 0.0 | 11 | 45.8 |
| VOMITING | 2 | 8.3 | 1 | 4.2 | 0 | 0.0 | 3 | 12.5 |

As can be seen from the results set forth in Table 3, there was only one incident of a moderate adverse event, and no incidents of severe adverse events reported by the test subjects during the application interval. Further, turning to FIG. 2, it can be seen that the level of dizziness, nausea and sleepiness significantly decreased after day 3 of the dosage interval. Other side effects such as headache, vomiting and constipation were also low in occurrence.

Table 4 provides a summary of the amount of drug which was measured as remaining in the patches which were removed from the subjects after 7 days.

TABLE 4

| AMOUNT LEFT IN PATCH (mg) | |
|---|---|
| MEAN | 8.59 |
| SE | 0.11 |
| % RELEASED (ASSAY) | |
| MEAN | 14.02 |
| SE | 1.08 |

Comparative Examples A–C

A three (3) treatment, randomized, crossover study was conducted in normal volunteers. The treatments consisted of Comparative Example A (a single application buprenorphine transdermal delivery system); Comparative Example B (a single dose of buprenorphine administered intravenously) and Comparative Example C (3 sequential applications, every three days, of the buprenorphine transdermal delivery system used in Comparative Example A). A 10–14 day washout period intervened between the first dosing (application) day of each treatment. For the buprenorphine transdermal delivery system, the wash-out started when the third sequential patch was removed. This study was not analytically blinded due to analytical chemistry considerations and different sampling times.

The buprenorphine transdermal delivery system (patch) used in Comparative Examples A and C contained 20 mg buprenorphine base, and is prepared in accordance with Example 1. It was contemplated that the buprenorphine patch of Comparative Examples A and C would provide approximately double the dose and approximately double the relative release rate as compared to the buprenorphine patch of Example 1. For Comparative Examples A and C, it was contemplated that approximately 1.2 mg buprenorphine would be released from the patch per day, which is equivalent to an intravenous dose of 0.3 mg every 6 hours. The reference buprenorphine intravenous injection (Comparative Example B) was 0.3 mg (Temgesic®) Injectable 0.3 mg/ml, [1 ml/vial]).

In Comparative Example A, the buprenorphine transdermal delivery system (single dose) was adhered to a relatively hairless area of a subject's right thorax at the level of the fifth intercostal space in the midaxillary line at approximately 8 am on day 1 and removed at approximately 8 am on day 4. For Comparative Example A (buprenorphine transdermal delivery system single dose), blood sampling was conducted as follows: Day 1: 0, (buprenorphine transdermal delivery system adhered) 2, 3, 4, 6, 8, 10, 12, and 16 hr; Day 2: 0, 6, 12 hr; Day 3: 0, 12 hr; Day 4: 0 (prior to removal), 0.25, 0.5, 0.75, 1, 2, 3, 6, 12 hr post-removal; Day 5: 0, 12 hr; Day 6: 0, 12 hr; Day 7: 0 hr With respect to Comparative Example B, buprenorphine intravenous (IV) injection, 0.3 mg was infused over 2 minutes at approximately 8 am on day 1 through an in-dwelling cannula in the right anticubital vein. The buprenorphine intravenous 0.3 mg blood sampling was conducted as follows: Day 1: 0, 1, 2, 3, 5, 10, 15, 20, 25, 30, 45 minutes and 1, 1.5, 2, 3, 4, 5, 6, 10, 12, 24 hr; arterial blood sampling (left radial artery) for the first 4 hours; venous blood sampling from 2 hours post-dose to 24 hours post-dose. Therefore arterial and venous blood sampling occurred simultaneously 2, 3 and 4 hours post-dose.

With respect to Comparative Example C, the buprenorphine transdermal delivery system (3 sequential applications), was adhered to a relatively hairless area of a subject's right thorax at the level of the fifth intercostal space in the midaxillary line at approximately 8 am on day 1 and removed at approximately 8 am on day 4. The second buprenorphine transdermal delivery system 50 µg/hr was placed just adjacent to the first patch after the first was removed on day 4 at approximately 8 am and removed on day 7 at approximately 8 am. The third buprenorphine transdermal delivery system 50 µg/hr was placed just adjacent to the second patch but not in the same place as the first patch after the second patch is removed on day 7 at approximately 8 am and removed on day 10 at approximately 8 am. Blood samples for Comparative Example C, buprenorphine transdermal delivery system 3 sequential applications, were obtained as follows: Day 1: 0, (buprenorphine transdermal delivery system adhered), 2, 3, 4, 6, 8, 10, 12, and 16 hr; Day 2: 0, 6, 12 hr; Day 3: 0, 12 hr; Day 4: 0 (prior to removal), and 2, 3, 4, 6, 8, 10, 12, 16 hrs (after second buprenorphine transdermal delivery system adhered); Day 5: 0, 6, 12 hr; Day 6: 0, 12 hr; Day 7: 0 (prior to removal), and 2, 3, 4, 6, 8, 10, 12, 16 hrs (after third buprenorphine transdermal delivery system adhered); Day 8: 0, 6, 12 hr; Day 9: 0, 12 hr; Day 10: 0 (prior to buprenorphine transdermal delivery system removal), and 0.25, 0.5, 0.75, 1, 2, 3, 6, 12 hr (post-removal); the wash-out period started after patch removal on Day 10; Day 11: 0, 12 hr; Day 12: 0, 12 hr; and Day 13: 0.

The pharmacokinetic variables determined for Comparative Examples A–C were as follows:

$AUC_{(0-last)}$: pg-hr/ml—The area under the curve, as calculated by the linear trapezoidal method, up to the last observed value;

$AUC_{inf}$: pg-hr/ml—The area under the curve, calculated using the linear trapezoidal method;

$C_{max}$: pg/ml—Maximum measured plasma buprenorphine over the time span specified;

$T_{max}$: hrs—Time of the maximum measured plasma buprenorphine; when the maximum value occurs in more than one time point, $T_{max}$ is defined as the first time point with this value;

$T_{(½)elm}$: The plasma half life of buprenorphine elimination, defined as $\ln 2/K_{elm}$, where $K_{elm}$ is the apparent first order elimination constant. The elimination rate constant was obtained from the slope of the terminal portion of the plasma-concentration time curve determined by regression analysis techniques;

$T_{(½)abs}$: The absorption half life of transdermal buprenorphine elimination, defined as $\ln 2/K_{abs}$, where $K_{abs}$ is the apparent first order absorption constant. Absorption rate was calculated only for the transdermal buprenorphine;

Cl: ml/min or 1/hr—Total clearance characterizes the clearing of the hypothetical plasma volume of drug per unit time;

$V_d$: 1 or 1/kg—Hypothetical volumes in which the drug is distributed in the body; and Absorption Rate: µg/hr—The rate at which buprenorphine enters the systemic circulation.

Plasma concentration data was analyzed using standard noncompartmental and compartmental techniques to derive pharmacokinetic parameters. In addition, various exploratory methods including fitting the intravenous data to pharmacokinetic models to determine which model best describes the data, and deconvolution analysis to determine the absorption rate was employed. Other parameters such as clearance, volumes of distribution, absorption rate, amount absorbed and bioavailability were determined by either standard noncompartmental or compartmental analysis or exploratory methods. The intravenous data was also analyzed utilizing compartmental modeling techniques.

A summary of plasma buprenorphine concentrations for Comparative Example A is provided in Table 5 below.

TABLE 5

Comparative Example A

| HOUR | MEAN PLASMA CONC. (pg/ml) | STD. DEV | CV % |
|---|---|---|---|
| 2 | 2.04 | 5.87 | 287.10 |
| 3 | 7.96 | 16.28 | 204.47 |
| 4 | 14.84 | 18.63 | 125.51 |
| 6 | 23.49 | 25.81 | 109.85 |
| 8 | 42.34 | 37.91 | 89.52 |
| 10 | 72.03 | 71.36 | 99.07 |
| 12 | 85.96 | 68.69 | 79.90 |
| 16 | 133.89 | 103.43 | 77.25 |
| 24 | 175.58 | 120.17 | 68.44 |
| 30 | 169.15 | 108.65 | 64.23 |
| 36 | 200.16 | 134.45 | 67.17 |
| 48 | 251.10 | 156.66 | 62.39 |
| 60 | 250.11 | 125.01 | 49.98 |
| 72 | 286.50 | 131.58 | 45.92 |
| 78 | 168.73 | 61.26 | 36.30 |
| 84 | 114.68 | 52.72 | 45.97 |
| 96 | 90.75 | 39.12 | 43.11 |
| 108 | 56.82 | 25.66 | 45.17 |
| 120 | 44.85 | 23.80 | 53.06 |
| 132 | 30.40 | 21.87 | 71.95 |
| 144 | 29.14 | 20.27 | 69.58 |

A summary of plasma buprenorphine concentrations (pg/ml) for Comparative Example C at each sampling time is set forth in Table 6 below:

TABLE 6

Comparative Example C

| HOUR | MEAN PLASMA CONC. (pg/ml) | STD. DEV | CV % |
|---|---|---|---|
| 2 | 0.54 | 2.63 | 489.90 |
| 3 | 5.70 | 13.18 | 231.23 |
| 4 | 10.33 | 14.64 | 141.71 |
| 6 | 28.84 | 31.19 | 108.31 |
| 8 | 54.62 | 65.83 | 120.52 |
| 10 | 78.92 | 81.23 | 102.93 |
| 12 | 95.14 | 75.70 | 79.57 |
| 16 | 162.26 | 114.80 | 70.75 |
| 24 | 218.57 | 153.58 | 70.27 |
| 30 | 206.10 | 141.70 | 68.75 |
| 36 | 205.08 | 110.76 | 54.01 |
| 48 | 265.04 | 123.66 | 46.66 |
| 60 | 256.18 | 133.48 | 52.11 |
| 72 | 306.02 | 152.77 | 49.92 |
| 74 | 278.22 | 135.14 | 48.57 |
| 75 | 245.91 | 112.66 | 45.82 |
| 76 | 237.01 | 83.41 | 35.19 |
| 78 | 213.54 | 94.42 | 44.22 |
| 80 | 215.45 | 103.75 | 48.15 |
| 82 | 216.00 | 107.68 | 49.85 |
| 84 | 210.52 | 107.67 | 51.14 |
| 88 | 219.77 | 110.46 | 50.26 |
| 96 | 269.91 | 134.61 | 49.87 |
| 102 | 205.54 | 102.03 | 49.64 |
| 108 | 225.11 | 87.97 | 39.08 |
| 120 | 310.27 | 153.57 | 49.50 |
| 132 | 300.34 | 157.05 | 52.29 |
| 144 | 305.99 | 159.75 | 52.21 |
| 146 | 301.39 | 141.37 | 46.91 |
| 147 | 289.96 | 132.91 | 45.84 |
| 148 | 287.68 | 151.93 | 52.81 |

TABLE 6-continued

Comparative Example C

| HOUR | MEAN PLASMA CONC. (pg/ml) | STD. DEV | CV % |
|---|---|---|---|
| 150 | 260.04 | 130.19 | 50.07 |
| 152 | 236.61 | 119.77 | 50.62 |
| 154 | 284.15 | 158.84 | 55.90 |
| 156 | 271.83 | 145.11 | 53.38 |
| 160 | 303.46 | 182.37 | 60.10 |
| 168 | 340.71 | 209.87 | 61.60 |
| 174 | 302.22 | 179.74 | 59.47 |
| 180 | 322.67 | 183.63 | 56.91 |
| 192 | 395.95 | 220.27 | 55.63 |
| 204 | 344.83 | 201.90 | 58.55 |
| 216 | 415.33 | 229.92 | 55.36 |
| 216.25 | 388.64 | 186.67 | 43.03 |
| 216.50 | 390.97 | 208.34 | 53.29 |
| 216.75 | 392.63 | 188.89 | 48.11 |
| 217 | 399.51 | 197.86 | 49.53 |
| 218 | 312.65 | 173.12 | 55.37 |
| 219 | 295.17 | 148.13 | 50.18 |
| 222 | 201.37 | 85.54 | 42.48 |
| 228 | 173.89 | 75.96 | 43.68 |
| 240 | 119.13 | 48.99 | 41.13 |
| 252 | 84.21 | 49.61 | 58.91 |
| 264 | 72.33 | 37.86 | 52.42 |
| 276 | 50.18 | 25.83 | 51.47 |
| 288 | 43.06 | 26.61 | 61.79 |

A summary of mean plasma buprenorphine concentrations (pg/ml) at each sampling time for Comparative Example B (buprenorphine intravenous 0.3 mg single dose) is provided in Table 7 below:

TABLE 7

Comparative Example B

| HOUR | MEAN PLASMA CONC. (pg/ml) | STD. DEV | CV % |
|---|---|---|---|
| 0.02 | 14812.04 | 11319.10 | 76.42 |
| 0.03 | 31052.04 | 16156.81 | 52.03 |
| 0.05 | 24547.00 | 16461.86 | 67.06 |
| 0.08 | 6418.80 | 1976.26 | 30.79 |
| 0.17 | 3360.76 | 2457.58 | 73.13 |
| 0.25 | 1747.96 | 465.81 | 26.65 |
| 0.33 | 1210.08 | 219.28 | 18.12 |
| 0.42 | 1050.00 | 242.10 | 23.06 |
| 0.50 | 931.52 | 207.25 | 22.25 |
| 0.75 | 692.92 | 175.29 | 25.30 |
| 1.00 | 584.40 | 148.93 | 25.48 |
| 1.50 | 457.44 | 131.44 | 28.73 |
| 2.00 | 335.12 | 79.36 | 23.68 |
| 3.00 | 238.80 | 63.03 | 26.39 |
| 4.00 | 170.87 | 49.84 | 29.17 |

A summary of the mean maximum concentration (Cmax) for Comparative Examples A–C measured in pg/ml is set forth in Table 8 below:

TABLE 8

$C_{max}$ Values for Comparative Examples A–C

| | Comparative Example A | Comparative Example C | Cmax (pg/ml) - Comparative Example B |
|---|---|---|---|
| Mean | 318.20 | 477.33 | 38635.56 |
| Std. Dev. | 151.24 | 216.92 | 14499.55 |

TABLE 8-continued

C$_{max}$ Values for Comparative Examples A–C

|  | Comparative Example A | Comparative Example C | Cmax (pg/ml) - Comparative Example B |
|---|---|---|---|
| Geometric Mean | 291.13 | 435.50 | 35251.92 |
| CV % | 47.53 | 45.44 | 37.53 |

A summary of mean Tmax values obtained for Comparative Examples A–C is set forth in Table 9 below:

TABLE 9

|  | Tmax Prior to Patch Removal (hrs) | | Tmax (hrs) |
|---|---|---|---|
|  | Comparative Example A | Comparative Example C | Comparative Example B |
| Mean | 61.92 | 168.39 | 0.04 |
|  | (out of 72 hrs total) | (out of 260 hrs total) |  |
| Std. Dev. | 13.27 | 42.68 | 0.01 |
| CV % | 21.43 | 25.35 | 26.26 |

Table 10 provides a summary of the area under the curve (AUC) (0-t) for Comparative Examples A–C:

TABLE 10

|  | Comparative Example A | Comparative Example C | Comparative Example B |
|---|---|---|---|
| Mean | 18,829.13 | 65,217.25 | 3,699.91 |
| Std. Dev. | 9,136.12 | 31,124.37 | 526.64 |
| Geometric Mean | 16,760.39 | 57,794.90 | 3,666.65 |
| CV % | 48.52 | 47.72 | 14.23 |

The pharmacodynamics were determined via VAS "drug effect" observations. The subject was asked "do you feel any of the drug?". The subject then rated the item by placing a vertical mark along a 100 mm visual analog scale (VAS) anchored on one end by "not at all" and on the other end by "an awful lot". The "drug effect" question was assessed just prior to each blood sample during the study. The following adverse effects were elicited just prior to blood sampling using the VAS: nausea; dizziness; and sleepiness. Asymmetric blood sampling was used in this study due to the number of sampling times.

Figure 3:
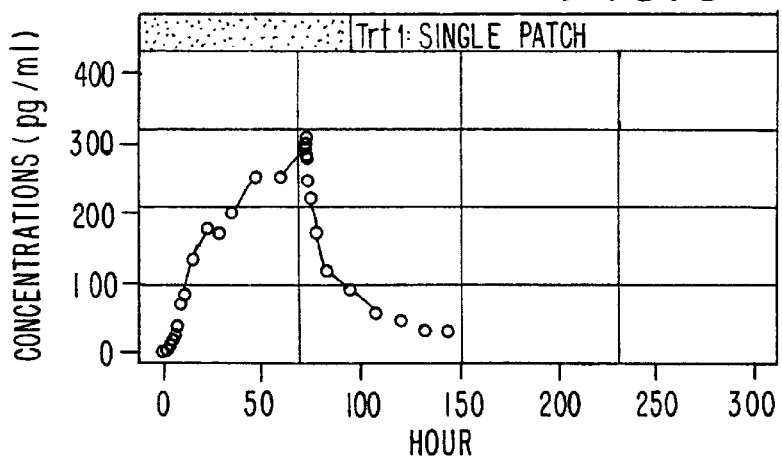
FIG. 3 is a graphical representation of the plasma concentration (pg/ml) over time (hours) for Comparative Example A.
Figure 4:
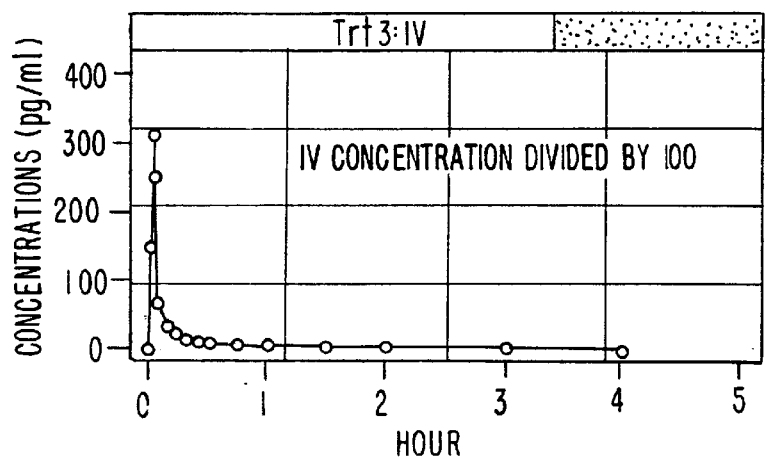
FIG. 4 is a graphical representation of the plasma concentration (pg/ml) over time (hours) for Comparative Example B (intravenous concentrations divided by 100)
Figure 5:
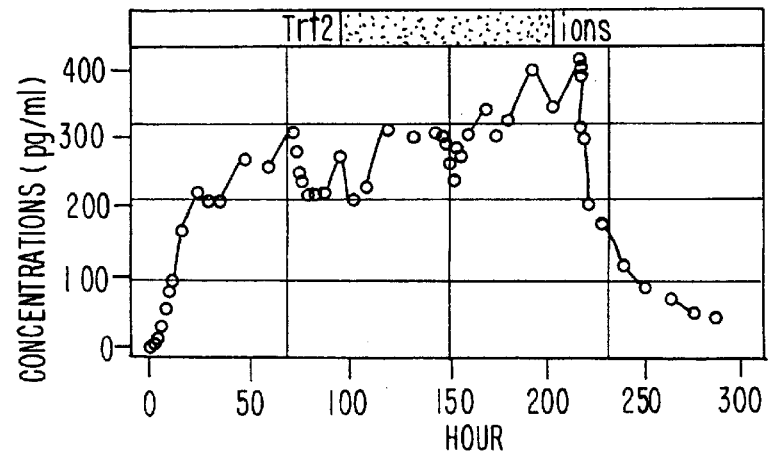
FIG. 5 is a graphical representation of the plasma concentration (pg/ml) over time (hours) for Comparative Example C.
Figure 6:
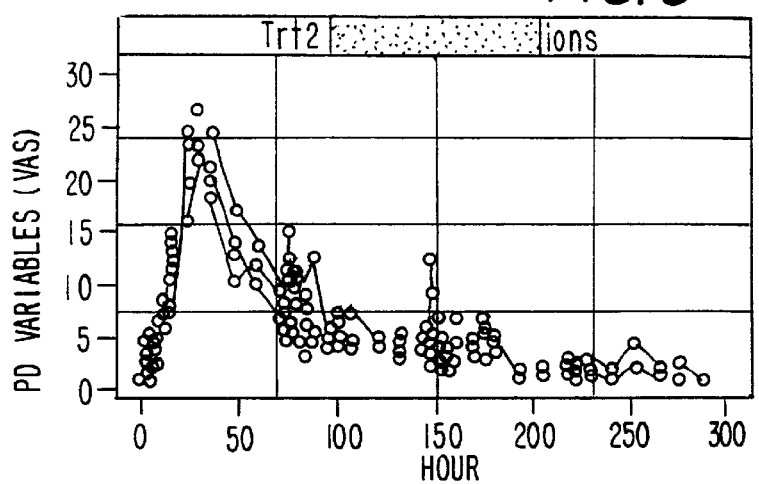
FIG. 6 is a graphical representation pharmacodynamic variables versus time (hours) for Comparative Example A.
Figure 7:
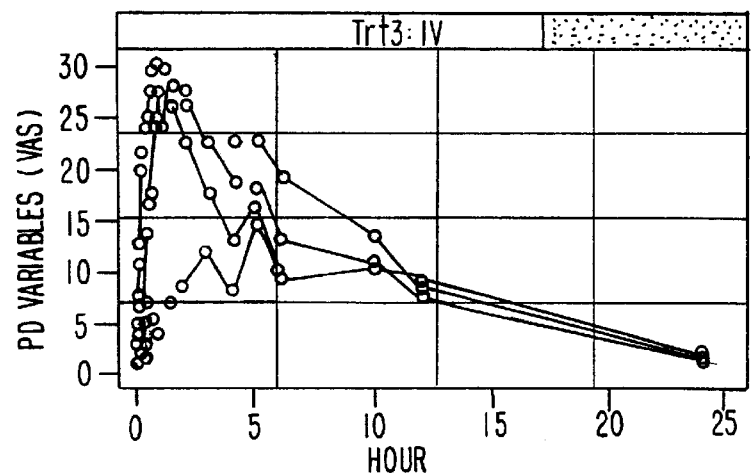
FIG. 7 is a graphical representation pharmacodynamic variables versus time (hours) for Comparative Example B.
Figure 8:
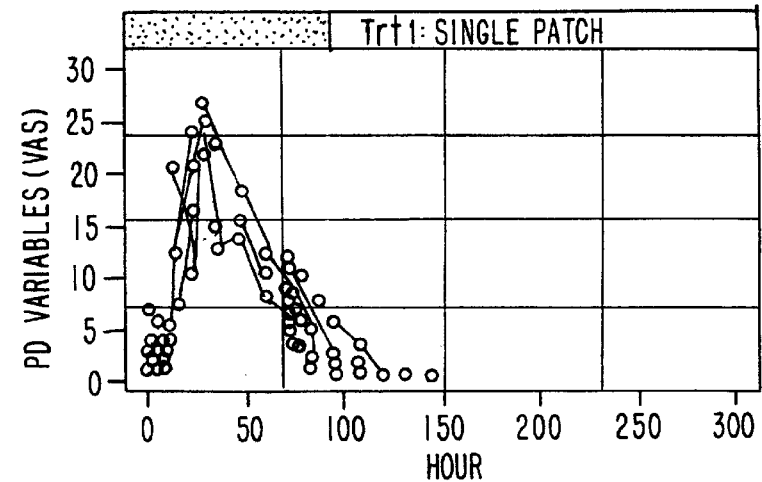
FIG. 8 is a graphical representation pharmacodynamic variables versus time (hours) for Comparative Example C.

The pharmacokinetic results (concentration in pg/ml vs. hours) for Comparative Examples A–C are depicted in FIGS. 3–5, respectively. FIG. 4 depicts the plasma concentration obtained divided by 100. The pharmacodynamic results (PD variables (VAS)) for Comparative Examples A–C are depicted in FIGS. 6–8, respectively.

Comparative Examples D–F

The bioequivalence between a buprenorphine transdermal delivery system in accordance with Example 1 is compared to identically prepared patches having different sizes and therefore different amounts of buprenorphine contained therein.

Comparative Example D ultilize a patch identical in size and contaiing the same amount of buprenorphine as Example 1. The total of buprenorphine included in the transdel patch is 10 mg, the active surface area is 12.5 cm$^2$ and the patch size is 30.6 cm$^2$. In Comparative Example E, two patches are utilized, each patch including total of buprenorphine of about 5 mg, and having an active surface area of 6.25 cm$^2$ and a patch size of 19.4 cm$^2$. Comparative Example F allows for the determination area of the dose proportionality of a buprenorphine transdermal delivery system (patch) having twice the dose as compared to Example 1. In Comparative Example F, the total of buprenorphine include in the transdermal patch is 20 mg, the active surface area is 25 cm$^2$ and the patch size is 51.8 cm$^2$. The study was conducted via a 3-way cross-over design. The patches were left in place for 72 hours and then removed.

Table 11 provides a summary of mean plasma buprenorphine concentrations (pg/ml) at each sampling time for Comparative Example D:

TABLE 11

| HOURS | MEAN PLASMA CONC. (pg/ml) | STD. DEV. | CV % |
|---|---|---|---|
| 3 | 1.92 | 8.82 | 458.26 |
| 6 | 22.69 | 30.98 | 136.54 |
| 9 | 38.54 | 48.79 | 126.62 |
| 12 | 59.22 | 62.92 | 106.24 |
| 16 | 89.85 | 78.93 | 87.84 |
| 24 | 128.70 | 72.79 | 56.55 |
| 30 | 125.99 | 84.68 | 67.21 |
| 36 | 143.07 | 78.40 | 54.80 |
| 48 | 196.72 | 101.50 | 51.59 |
| 60 | 182.72 | 82.61 | 45.21 |
| 72 | 169.95 | 65.04 | 38.27 |
| 84 | 122.19 | 41.69 | 34.12 |
| 96 | 83.30 | 35.56 | 42.69 |
| 108 | 55.09 | 30.82 | 55.94 |
| 120 | 41.63 | 20.74 | 49.82 |
| 132 | 27.14 | 25.47 | 93.84 |
| 144 | 17.54 | 20.09 | 114.51 |

Table 12 provides a summary of the pharmacokinetic parameters for Comparative Example D:

TABLE 12

| PARAMETER | ARITHMETIC MEAN (SE) | GEOMETRIC MEAN (SE) |
|---|---|---|
| AUC (0-Infinity) | 16278.05 (1246.6) | 15255.84 (1272.5) |
| AUC (0-Last) | 14446.10 (1292.0) | 13162.96 (1340.6) |
| Cmax (pg/ml) | 229.87 (19.29) | 214.47 (17.92) |
| T ½ Elim. (hrs) | 30.53 (2.80) |  |
| Tmax (hrs) | 67.02 (3.14) |  |

Table 13 provides a summary of mean plasma buprenorphine concentrations for Comparative Example E:

TABLE 13

| HOURS | MEAN PLASMA CONC. (pg/ml) | STD. DEV. | CV % |
|---|---|---|---|
| 3 | 1.63 | 7.29 | 447.21 |
| 6 | 19.61 | 33.28 | 169.70 |
| 9 | 29.09 | 44.04 | 151.40 |
| 12 | 44.43 | 56.91 | 128.09 |
| 16 | 59.77 | 66.25 | 110.86 |
| 24 | 110.49 | 98.86 | 89.48 |
| 30 | 107.58 | 86.83 | 80.71 |
| 36 | 116.36 | 83.01 | 71.34 |
| 48 | 154.35 | 83.40 | 54.03 |
| 60 | 151.22 | 90.70 | 59.98 |
| 72 | 145.20 | 62.84 | 43.28 |
| 84 | 106.91 | 38.86 | 36.35 |
| 96 | 82.61 | 34.87 | 42.21 |
| 108 | 44.83 | 26.74 | 59.65 |
| 120 | 29.68 | 24.26 | 81.73 |

TABLE 13-continued

| HOURS | MEAN PLASMA CONC. (pg/ml) | STD. DEV. | CV % |
|---|---|---|---|
| 132 | 22.52 | 24.42 | 108.44 |
| 144 | 9.24 | 17.28 | 186.93 |

Table 14 provides a summary of the pharmacokinetic parameters for Comparatve Example E:

TABLE 14

| PARAMETER | ARITHMETIC MEAN (SE) | GEOMETRIC MEAN (SE) |
|---|---|---|
| AUC (0-Infinity) | 13450.96 (1326.8) | 12315.56 (1142.0) |
| AUC (0-Last) | 12026.65 (1318.7) | 10796.23 (1110.3) |
| Cmax (pg/ml) | 199.10 (17.50) | 186.49 (14.69) |
| T ½ Elim. (hrs) | 25.82 (1.51) | |
| Tmax (hrs) | 68.26 (3.18) | |

Table 15 provides a summary of mean plasma buprenorphine concentrations for Comparative Example F:

TABLE 15

| HOURS | MEAN PLASMA CONC. (pg/ml) | STD. DEV. | CV % |
|---|---|---|---|
| 3 | 5.23 | 13.21 | 252.44 |
| 6 | 34.49 | 55.11 | 159.80 |
| 9 | 58.67 | 91.17 | 155.40 |
| 12 | 94.52 | 111.07 | 117.51 |
| 16 | 137.07 | 118.65 | 86.56 |
| 24 | 195.58 | 148.53 | 75.94 |
| 30 | 201.51 | 142.24 | 70.59 |
| 36 | 229.52 | 154.25 | 67.20 |
| 48 | 283.35 | 124.06 | 43.78 |
| 60 | 314.17 | 173.81 | 55.32 |
| 72 | 306.60 | 124.57 | 40.63 |
| 84 | 209.66 | 62.84 | 29.97 |
| 96 | 143.30 | 43.88 | 30.62 |
| 108 | 113.53 | 70.33 | 61.95 |
| 120 | 78.71 | 37.46 | 47.59 |
| 132 | 75.29 | 47.92 | 63.64 |
| 144 | 44.45 | 32.26 | 72.57 |

Table 16 provides a summary of the dose-corrected pharmacoldnetic parameters for Comparative Example F. The values are calculated based on a Cmax value which is one-half the actual reported value:

TABLE 16

| PARAMETER | ARITHMETIC MEAN (SE) | GEOMETRIC MEAN (SE) |
|---|---|---|
| AUC (0-Infinity) | 14761.59 (1469.7) | 13540.78 (1228.3) |
| AUC (0-Last) | 12558.04 (1313.9) | 11456.76 (1067.0) |
| Cmax (pg/ml) | 191.84 (16.93) | 179.60 (14.23) |
| T ½ Elim. (hrs) | 26.59 (1.52) | |
| Tmax (hrs) | 72.37 (1.89) | |

Table 17 provides a summary of the buprenorphine patch residuals for each of Comparative Examples D–F:

TABLE 17

SUMMARY OF BUPRENORPHINE PATCH RESIDUALS

| | Ex. D | Ex. F | Ex. E |
|---|---|---|---|
| AMOUNT LEFT IN PATCH (mg) | | | |
| N | 27 | 27 | 52 |
| MEAN | 8.76 | 18.31 | 4.75 |
| SE | 0.07 | 0.15 | 0.03 |
| % RELEASED (ASSAY) | | | |
| N | 27 | 27 | 52 |
| MEAN | 12.31 | 10.84 | 8.43 |
| SE | 0.67 | 0.73 | 0.53 |

Figure 12:
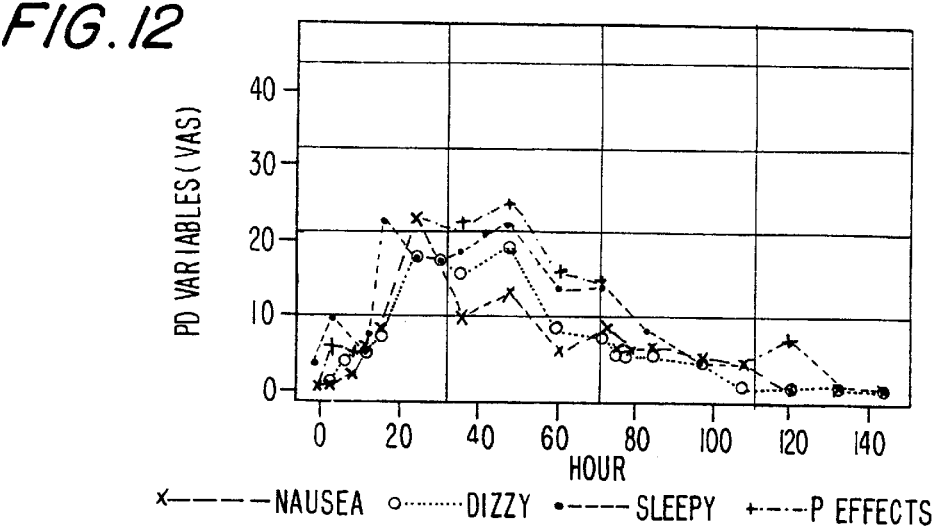
FIG. 12 is a graphical representation pharmacodynamic variables versus time (hours) for Comparative Example D.
Figure 13:
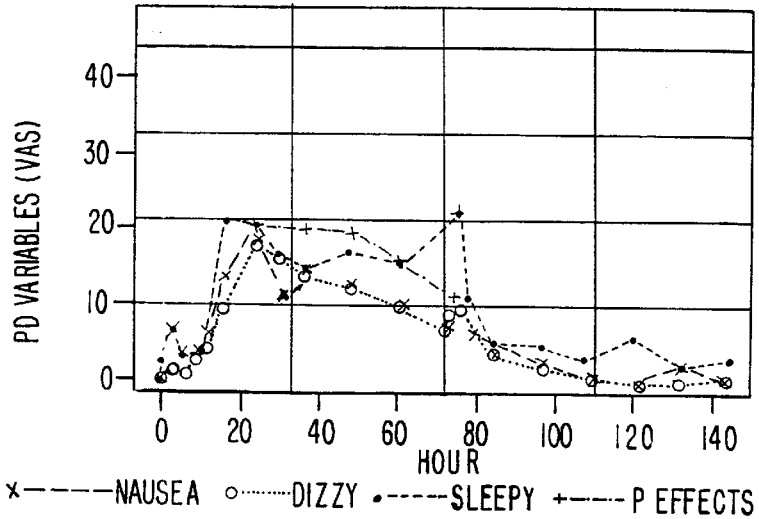
FIG. 13 is a graphical representation pharmacodynamic variables versus time (hours) for Comparative Example E.
Figure 14:
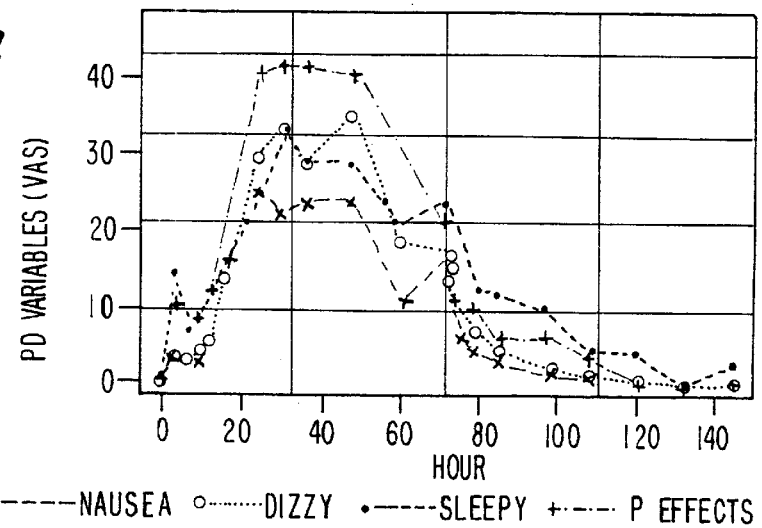
FIG. 14 is a graphical representation pharmacodynamic variables versus time (hours) for Comparative Example F.

The pharmacokinetic results (concentration in pg/ml vs. hours) for Comparative Examples D–F are depicted in FIGS. 9–11, respectively. The pharmacodynamic results (PD variables (VAS)) for Comparative Examples A–C are depicted in FIGS. 12–14, respectively.

Conclusions

In order to readily consider the results obtained comparing the method of the present invention to the Comparative Examples, the following tables are provided.

Table 18 provides a direct comparison of the plasma concentrations obtained from Example 1 (a 10 mg buprenorphine patch maintained in contact with the subjects' skin for 7 days) to Compaive Example A (20 mg buprenorphine patch left on the subjects' skin for only 3 days, then removed) to Comparative Example C (three sequential applications of a 20 mg buprenorphine patch left on the subjects' skin for only 3 days, then removed). In order to compare the plasma concetrations, the plasma concentrations of Comparative Examples A and C are also presented at 50% concentrations for each time interval:

TABLE 18

COMPARISON OF PLASMA CONCENTRATIONS

| HOUR/ (DAY) | Ex. 1 MEAN | COMPARATIVE EXAMPLE C | | COMPARATIVE EXAMPLE A | |
|---|---|---|---|---|---|
| | | MEAN | MEAN (½ DOSE) | MEAN | MEAN (½ DOSE) |
| 24 (1) | 58.94 | 218.57 | 109.29 | 175.58 | 87.79 |
| 48 (2) | 104.69 | 265.04 | 132.52 | 251.10 | 125.55 |
| 72 (3) | 130.55 | 306.02 | 153.01 | 286.50 | 143.25 |
| 96 (4) | 146.70 | 269.91 | 134.96 | 90.75 | 45.38 |
| 120 (5) | 136.22 | 310.27 | 155.14 | 44.85 | 22.43 |
| 144 (6) | 115.23 | 305.99 | 153.00 | 29.14 | 14.57 |
| 168 (7) | 102.00 | 340.71 | 170.36 | | |
| 192 (8) | | 395.95 | 197.98 | | |

The data presented in Table 18 shows that, surprisingly, plasma levels effective to provide analgesia were present in Example 1 (patch remained on skin for 7 days) even 7 days after application of the patch; whereas in Comparative Example A (patch removed after 3 days), blood levels fell dramatically once the patch was removed, such that plasma levels which would be indicative of ineffective treaatment for the dosage of buprenorphine occurred not long after patch removal. On the other hand, turning to Comparative Example C, it is apparent that the plasma levels obtained from 3-day sequential administration of the buprenorphine patch resulted in significant increases in Cmax levels during each day dosing interval. This fact is confirmed by the graph of plasma concentration over time for Comparative Example C provided in FIG. 3. In contrast, the plasma level for Example 1 remained substantially level over the time-frame of 72 hours–168 hours after patch application. The results indicate that the method of the present invention has the surprising benefit of reducing total plasma concentrations of buprenorphine required to allow patients to experience effective analgesia. Furthermore, comparing the VAS reselts graphically depicted for Example 1 to Comparative Example C, it is apparent that side effects were significantly reduced according to the method of Example 1, during the 7-day dosage interval. Further benefits are obtained from the invention respect to modes of administration other than trasdermally where the large plasma concentration peaks obtained in the prior art, e.g., through intravenous dosing, can be avoided. For example, in Comparative Example B, a Cmax in excess of about 30,000 pg/ml was obtained.

Table 19 provides a direct comparison of the plasma concenrations of Example 1 (a 10 mg buprenorphine patch maintained in contact with the subjects' skin for 7 days) to Comparative Example D (same 10 mg buprenorphine patch left on the subjects' skin for only 3 days, then removed) to Comparative Example E (two 5 mg buprenorphine patches left on the subjects' skin for only 3 days, then removed):

result is surprising in view of the fact that the patches are designed to provide effective analgetic levels of buprenorphine only for a three day period—these patches are not designed to provide effective plasma levels of buprenorphine over a substantially longer period of time. (It must be noted that the absolute mean plama levels of Example 1 and the Comparative Examples are not directly comparable because these results are taken from different studies involving different subjects, etc.).

Further surprising results are apparent from the data provided in Table 20 below, which compares the amount of buprenorphine retained in the transdermal delivery systems in Example 1 to certain Comparative Examples, as well as their relative release rates:

TABLE 20

BUPRENORPHINE PATCH RELEASE RATES

| Patch strength | Example | cum. amt. released [mg] | RR [mg/patch/day] 3 days appl. | RR [mg/patch/day] 7 days appl. | $RR_{norm}$ [mg/cm$^2$/day] |
|---|---|---|---|---|---|
| 5 MG | E | 0.44 mg | 0.146 | — | 0.0234 |
| 10 MG | D | 1.23 mg | 0.410 | — | 0.0328 |
| 20 MG | F | 2.52 mg | 0.742 | — | 0.0297 |
| 20 MG | A, C | 3.21 mg | 1.090 | — | 0.0437 |
| 10 MG | 1 | 1.40 mg | — | 0.200 | 0.160 |

RR = relative release rate

TABLE 19

COMPARISON OF PLASMA CONCENTRATIONS (PG/ML)

| Hours (Post-Application) | Ex. 1 MEAN CONC. | Ex. D MEAN CONC. | Ex. E MEAN CONC. |
|---|---|---|---|
| 3 | | 1.92 | 1.63 |
| 6 | 1.76 | 22.69 | 19.61 |
| 9 | | 38.54 | 29.09 |
| 12 | 18.47 | 59.22 | 44.43 |
| 16 | | 89.85 | 59.77 |
| 24 | 58.94 | 128.70 | 110.49 |
| 30 | 67.69 | 125.99 | 107.58 |
| 36 | 82.44 | 143.07 | 116.36 |
| 48 | 104.69 | 196.72 | 154.35 |
| 60 | 112.93 | 182.72 | 151.22 |
| 72 | 130.55 | 169.95 | 145.20 |
| 84 | 129.03 | 122.19 | 106.91 |
| 96 | 146.70 | 83.30 | 82.61 |
| 108 | 135.49 | 55.09 | 44.83 |
| 120 | 136.22 | 41.63 | 29.68 |
| 132 | 124.78 | 27.14 | 22.52 |
| 144 | 115.23 | 17.54 | 9.24 |

The results depicted in Table 19 confirm that the method according to the present invention provides effective plasma levels over the 7-day period; whereas if the patch (or patches) containing the same dose is removed after 3 days, the buprenorpbine plasma levels fall precipitously over the next 24 hour interval to levels which would be indicative of ineffective treatment for the dosage of buprenorphine. This The total amount of buprenorphine released for Example 1 (1.40 mg) may be expressed as 0.2 mg buprenorphine administered per day, when averaged over the seven day dosing interval. In contrast, Comparative Example E (same patch over 3 days) released a total of 1.23 mg, which may be expressed as 0.41 mg buprenorphine admninistered per day. Comparing the cumulative amount released for Example 1 as compared to Comparative Example D, it can be seen that the present invention results in one-half the dose (mg/patch/day) which would be administered based on prior art methodology. Further, it is apparent that almost all of the buprenorphine dose for Example 1 is released over the first 72 hours (3 days)—1.23 mg released from the 10 mg patch over 3 days is 87.86% of the 1.4 mg released from the same patch over 7 days. It is surprising that analgesia can be maintained given the very low amount of buprenorphine released from the 10 mg patch over the 72–168 hour dosing interval.

Further, the results indicate that over the first 72 hours the buprenorphine is released substantially according to first order kinetics, whereas during the 72–168 hour time period after administration, the buprenorphine is released substantially according to zero order kinetics. This is confirmed from the plasma concentration curve provided for Example 1 in FIG. 1. Thus, during the first 72 hours after administration according to the invention, a relative release rate of 17.1 ug/br is obtained (1.23 mg divided by 72 hours); whereas from 72–168 hours after administration according to the invention, the relative release rate maybe lowered to only 1.77 ug/hr (1.40 mg minus 1.23 mg=0.17 mg divided by 96 hours) while maintaining effective analgtic levels of buprenorphine in human patients.

EXAMPLE 2

In Example 2, the method of the present invention is accomplished via a different mode of administration, i.e., intravenous infusion. The pattern of plasma concentrations seen through time in this invention can be achieved by using an intravenous infusion using the injectable, parenteral form of, e.g., buprenorphine hydrochloride suitably diluted in an intravenous infusion solution. The infusion rate would be controlled by a programable infusion pump, to provide the desired plasma concentration profile. The rate of infusion through time can be determined and adjusted based upon pharmacodynamic parameters such as pupil size (pupilometry) or pain relief (analgesia) or by the results of a suitable bioassay to determine the plasma buprenorphine concentrations at any particular point in time. In addition, it is possible to model the desired curve using pharmacokinetic modeling techniques; in this way the desired curve can be approximated without need for pharmacoldnetic or pharmacodynamic monitoring. However, periodic plasma concentration determations would make the model more accurate and allow further adjustment of the infusion rate.

Following the method set forth above, mean plasma concentrations are obtained as follows: a mean plasma concentration from about 1 to about 28 pg/ml at about 6 hours after initiation of the dosing interval; a mean plasma concentration from about 14 to about 74 pg/ml at about 12 hours after initiation of the dosing interval; a mean plasma concentration from about 30 to about 161 pg/ml at about 24 how after initiation of the dosing integral; a mean plasma concentration from about 51 to about 188 pg/ml at about 36 hours after initiation of the dosing interval; a mean plasma concentration from about 62 to about 246 pg/ml at about 48 hours after initiation of the dosing interval; a mean plasma concentration from about 79 to about 246 pg/ml at about 60 hours after initiation of the dosing interval; a mean plasma concentration from about 85 to about 263 pg/ml at about 72 hours after initiation of the dosing interval; a mean plasma concentration from about 92 to about 263 pg/ml at about 96 hours after initiation of the dosing a mean plasma concentration from about 94 to about 263 pg/ml at about 120 hours after initiaton of the dosing interval; a mean plasma concentration from about 86 to about 243 pg/ml at about 144 hours after initiation of the dosing interval; and a mean plasma concentration from about 77 to about 210 pg/ml at about 168 hours after initiation of the dosing interval (for a seven day dosing interval).

It will be readily apparent that various modifications to the invention may be made by those skilled in the art without departing from the scope of this invention. For example, many different transdermal delivery systems may be utilized in order to obtain the relative release rates and plasma levels described herein. Further, it is possible that mean values for plasma concentrations over a particular patient population for a particular described time point along the dosing interval may vary from the plasma concentration ranges described herein for that time point. Such obvious modifications are considered to be within the scope of the appended claims.

What is claimed is:

1. A method of treating human patients suffering from opioid addiction by applying a transdermal delivery system containing buprenorphine onto the skin of the patient and maintaining the transdermal delivery system in contact with the skin for a 3 day dosing interval, the transdermal delivery system containing an amount of buprenorphine sufficient to maintain an adequate relative release rate to provide a plasma concentration of from about 1000 pg/ml to about 10,000 pg/ml at the end of said 3 day dosing interval, and maintaining the transdermal delivery system in contact with the patient's skin for at least 2 to about 5 additional days beyond said 3:day dosing interval, such that the patient continues to receive effective treatment for opioid addiction from said transdermal buprenorphine delivery system over said dosing interval.

2. The method of claim 1, wherein the plasma concentration attained at the end of said 3 day dosing interval is from about 5000 pg/ml to about 8000 pg/ml.

3. The method of claim 1 wherein said patch is maintained on the skin of the patient for about 7 days.

4. The method of claim 1 wherein said transdermal patch provides a substantially first order plasma level increase of buprenorphine from the initiation of the dosing interval until about 72 hours after the initiation of the dosing interval.

5. The method of claim 1 wherein said transdermal patch provides substantially zero order plasma level fluctuation of buprenorphine from about 72 hours after the initiation of the dosing interval until the end of at least the five-day dosing interval.

6. The method of claim 1 wherein said transdermal patch provides a substantially first order plasma level increase of buprenorphine from the initiation of the dosing interval until about 72 hours after the initiation of the dosing interval and provides a substantially zero order plasma level fluctuation of buprenorphine from about 72 hours after the initiation of the dosing interval until the end of at least the five-day dosing interval.

7. The method of claim 5 wherein the plasma level of buprenorphine at 72 hours does not decrease by more than 30% over the next 48 hours.

8. The method of claim 5 wherein said patch is maintained on the skin of the patient for about 7 days.

9. The method of claim 8 wherein the plasma level of buprenorphine at 120 hours does not decrease by more than 30% over the next 48 hours.

10. A method of treating pain in a human patient comprising
   administering an opioid transdermally to said human patient by applying a transdermal delivery system to the skin of a patient, and maintaining said transdermal delivery system in contact with the skin of said patient for at least 5 days, said transdermal delivery system providing a substantially first order plasma level increase of said opioid from the initiation of the dosing interval until about 72 hours after the initiation of the dosing interval and providing a substantially zero order plasma level fluctuation of said opioid from about 72 hours after the initiation of the dosing interval until the end of at least the five-day dosing interval.

11. The method of claim 10 wherein said opioid is buprenorphine.

* * * * *